(12) United States Patent
Watanabe et al.

(10) Patent No.: US 11,033,382 B2
(45) Date of Patent: Jun. 15, 2021

(54) INTRAOCULAR LENS INJECTOR

(71) Applicant: Hoya Corporation, Tokyo (JP)

(72) Inventors: Yoshitaka Watanabe, Tokyo (JP); Kazunori Kudo, Saku (JP)

(73) Assignee: Hoya Corporation, Tokyo (JP)

( * ) Notice: Subject to any disclaimer, the term of this patent is extended or adjusted under 35 U.S.C. 154(b) by 172 days.

(21) Appl. No.: 16/313,184

(22) PCT Filed: Jun. 28, 2017

(86) PCT No.: PCT/JP2017/023749
§ 371 (c)(1),
(2) Date: Dec. 26, 2018

(87) PCT Pub. No.: WO2018/003854
PCT Pub. Date: Jan. 4, 2018

(65) Prior Publication Data
US 2019/0151078 A1 May 23, 2019

(30) Foreign Application Priority Data

Jun. 28, 2016 (JP) .............................. JP2016-127295

(51) Int. Cl.
*A61F 9/007* (2006.01)
*A61F 2/16* (2006.01)
(52) U.S. Cl.
CPC ................ *A61F 2/167* (2013.01); *A61F 2/16* (2013.01); *A61F 2/1678* (2013.01); *A61F 9/007* (2013.01)
(58) Field of Classification Search
CPC ...... A61F 2/1662; A61F 6/1664; A61F 2/167; A61F 2/1667; A61F 2/1672; A61F 2/1678; A61F 9/007; A61F 2/16
See application file for complete search history.

(56) References Cited

U.S. PATENT DOCUMENTS 2,761,446 A 9/1956 Reed
3,212,685 A 10/1965 Swan
(Continued)

FOREIGN PATENT DOCUMENTS

DE 3610925 10/1987
DE 4110278 10/1992
(Continued)

OTHER PUBLICATIONS

EPO Extended European Search Report dated Feb. 5, 2020 for EPO App. Ser. No. 17820208.1.
(Continued)

*Primary Examiner* — Kathleen S Holwerda
(74) *Attorney, Agent, or Firm* — Henricks Slavin LLP

(57) ABSTRACT

There is provided an intraocular lens injector including: a hollow body composed of an injector main body 5 having a lens installing portion on which an intraocular lens is installed, and an injection tube 7 attached to a tip part of the injector body 5; a rotary member 8 having a first threaded portion formed thereon and attached to a rear end part of the injector body 5 that constitutes the hollow body, rotatably around an axis of the hollow body; a plunger 9 having a second threaded portion 9c formed thereon, and configured to move through the hollow body in an axial direction of the hollow body; a rod 10 configured to push out the intraocular lens from the lens installing portion by moving through the hollow body in the axial direction of the hollow body together with the plunger 9, wherein a tip side of the plunger 9 is injected into the hollow body in a state in which the first threaded portion and the second threaded portion 9c are meshed with each other, and a rear end side of the plunger 9 is disposed in a state of protruding backward of the rotary member 8.

21 Claims, 31 Drawing Sheets

(56) References Cited

U.S. PATENT DOCUMENTS

| | | |
|---|---|---|
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,050,999 A | 4/2000 | Paraschac et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,605,093 B1 | 8/2003 | Blake |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |

(56) References Cited

U.S. PATENT DOCUMENTS

| | | |
|---|---|---|
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,749,631 B1 | 6/2004 | Pietrini et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,526 B2 | 7/2013 | Pynson |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 9,289,288 B2 | 3/2016 | Someya et al. |
| 9,314,373 B2 | 4/2016 | Kudo et al. |
| 9,326,847 B2 | 5/2016 | Sanger |
| 9,364,320 B2 | 6/2016 | Ichinohe et al. |
| 9,554,894 B2 | 1/2017 | Inoue |
| 9,572,710 B1 | 2/2017 | Kudo et al. |
| 9,655,718 B2 | 5/2017 | Kudo |
| 9,687,340 B2 | 6/2017 | Anderson |
| 9,877,826 B2 | 1/2018 | Kudo et al. |
| 9,901,442 B2 | 2/2018 | Kudo et al. |
| 9,907,647 B2 | 3/2018 | Inoue |
| 9,980,811 B2 | 5/2018 | Kudo et al. |
| 10,039,668 B2 | 8/2018 | Kudo et al. |
| 10,383,723 B2 | 8/2019 | Kudo |
| 10,390,940 B2 | 8/2019 | Someya et al. |
| 10,405,971 B2 | 9/2019 | Someya et al. |
| 10,517,717 B2 | 12/2019 | Inoue |
| 10,799,339 B2 | 10/2020 | Kudo et al. |
| 10,849,738 B2 | 12/2020 | Kudo et al. |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin et al. |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212408 A1 | 11/2003 | Kobayashi |
| 2003/0212409 A1 | 11/2003 | Kobayashi et al. |
| 2004/0039345 A1 | 2/2004 | Benz et al. |
| 2004/0111094 A1 | 6/2004 | Meyer |
| 2004/0117012 A1 | 6/2004 | Vincent |
| 2004/0127911 A1 | 7/2004 | Figueroa et al. |
| 2004/0147938 A1 | 7/2004 | Dusek et al. |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek et al. |
| 2006/0142781 A1 | 6/2006 | Pynson et al. |
| 2006/0167466 A1 | 7/2006 | Dusek |
| 2006/0200167 A1 | 9/2006 | Peterson et al. |
| 2006/0229633 A1 | 10/2006 | Shepherd |
| 2006/0235429 A1 | 10/2006 | Lee et al. |
| 2006/0293694 A1 | 12/2006 | Futamura |
| 2007/0005135 A1 | 1/2007 | Makker et al. |
| 2007/0168026 A1 | 7/2007 | Nagasaka |
| 2007/0270945 A1 | 11/2007 | Kobayashi |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2009/0270876 A1 | 10/2009 | Hoffmann et al. |
| 2009/0292293 A1 | 11/2009 | Bogaert et al. |
| 2010/0082037 A1 | 4/2010 | Kobayashi et al. |
| 2010/0094309 A1 | 4/2010 | Hboukhny et al. |
| 2010/0106160 A1 | 4/2010 | Tsai |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2010/0331808 A1 | 12/2010 | Py et al. |
| 2011/0046633 A1 | 2/2011 | Pankin et al. |
| 2011/0046635 A1 | 2/2011 | Pankin et al. |
| 2011/0082463 A1 | 4/2011 | Inoue |
| 2011/0098717 A1 | 4/2011 | Inoue |
| 2011/0144654 A1 | 6/2011 | Isaacs et al. |
| 2011/0172676 A1 | 7/2011 | Chen |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022548 A1* | 1/2012 | Zacharias ............ A61F 2/1672 606/107 |
| 2012/0022549 A1 | 1/2012 | Someya et al. |
| 2012/0071887 A1 | 3/2012 | Ichinohe et al. |
| 2012/0123438 A1 | 5/2012 | Horvath et al. |
| 2013/0006259 A1 | 1/2013 | Sanger |
| 2013/0018460 A1 | 1/2013 | Anderson |
| 2013/0085507 A1 | 4/2013 | Nagasaka |
| 2013/0226193 A1 | 8/2013 | Kudo et al. |
| 2013/0245635 A1 | 9/2013 | Inoue |
| 2013/0345713 A1 | 12/2013 | Cole et al. |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |
| 2014/0135784 A1 | 5/2014 | Maroscheck |

(56) References Cited

U.S. PATENT DOCUMENTS

| | | |
|---|---|---|
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |
| 2014/0276901 A1 | 9/2014 | Auld |
| 2015/0327992 A1 | 11/2015 | Wagner et al. |
| 2016/0000556 A1 | 1/2016 | Perera |
| 2016/0113759 A1 | 4/2016 | Inoue |
| 2016/0151150 A1 | 6/2016 | Sato |
| 2016/0193038 A1 | 7/2016 | Kudo et al. |
| 2016/0256316 A1 | 9/2016 | Van Noy et al. |
| 2016/0270907 A1 | 9/2016 | Attinger |
| 2016/0331587 A1 | 11/2016 | Yamada et al. |
| 2016/0346077 A1 | 12/2016 | Someya et al. |
| 2017/0079772 A1 | 3/2017 | Kudo |
| 2017/0151056 A1 | 6/2017 | Inoue |
| 2017/0202662 A1 | 7/2017 | Someya et al. |
| 2017/0252149 A1 | 9/2017 | Kudo et al. |
| 2017/0252150 A1 | 9/2017 | Kudo et al. |
| 2017/0258582 A1 | 9/2017 | Kudo et al. |
| 2017/0354493 A1 | 12/2017 | Andersen et al. |
| 2018/0014996 A1 | 1/2018 | Asbaghi |
| 2018/0250125 A1 | 9/2018 | Kudo et al. |
| 2018/0353287 A1 | 12/2018 | Kudo et al. |
| 2019/0192284 A1 | 6/2019 | Watanabe et al. |
| 2020/0113674 A1 | 4/2020 | Someya et al. |

FOREIGN PATENT DOCUMENTS

| | | |
|---|---|---|
| DE | 19544119 A1 | 5/1997 |
| EP | 0363213 | 4/1990 |
| EP | 0727966 | 9/2003 |
| EP | 1360947 A1 | 11/2003 |
| EP | 1502559 A1 | 7/2004 |
| EP | 1808150 A1 | 7/2007 |
| EP | 1832247 A1 | 9/2007 |
| EP | 1338254 | 12/2008 |
| EP | 2074961 A1 | 7/2009 |
| EP | 2255751 A1 | 12/2010 |
| EP | 2286763 A1 | 2/2011 |
| EP | 2286764 A1 | 2/2011 |
| EP | 2574308 A2 | 4/2013 |
| EP | 2853236 A2 | 4/2015 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2001-259033 | 9/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-527162 A | 9/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-244570 A | 9/2007 |
| JP | 2007-526091 A | 9/2007 |
| JP | 2007-307168 A1 | 11/2007 |
| JP | 2007-533379 A | 11/2007 |
| JP | 2008-521535 A | 6/2008 |
| JP | 2008-212689 A | 9/2008 |
| JP | 2011-502012 A | 1/2011 |
| JP | 2016-137122 A | 8/2016 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO2002071982 A1 | 9/2002 |
| WO | WO2002096322 A1 | 12/2002 |
| WO | WO2004/041323 A2 | 5/2004 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |
| WO | WO2012086797 A1 | 6/2012 |
| WO | WO2012155887 A1 | 11/2012 |
| WO | WO2015012312 A1 | 1/2015 |

OTHER PUBLICATIONS

PCT Written Opinion dated Oct. 3, 2017 for PCT App. Ser. No. PCT/JP2017/023749.

U.S. Appl. No. 15/063,395, filed Mar. 7, 2016, US 20160346077A1.

U.S. Appl. No. 15/476,717, filed Mar. 31, 2017, US 20170202662A1.

U.S. Appl. No. 15/382,377, filed Dec. 16, 2016, US 20170151056A1.

U.S. Appl. No. 13/061,143, filed Feb. 26, 2011, U.S. Pat. No. 8,470,032.

U.S. Appl. No. 15/126,277, filed Sep. 14, 2016, US 20170079772A1.

U.S. Appl. No. 15/756,565, filed Feb. 28, 2018, US 20180250125A1.

U.S. Appl. No. 15/756,569, filed Feb. 28, 2018, US 20180353287A1.

U.S. Appl. No. 12/602,442, filed Dec. 15, 2009, U.S. Pat. No. 8,747,465.

U.S. Appl. No. 13/244,449, filed Sep. 24, 2011, U.S. Pat. No. 9,289,288.

U.S. Appl. No. 15/063,395, filed Mar. 7, 2016, U.S. Pat. No. 10,390,940.

U.S. Appl. No. 15/476,717, filed Mar. 31, 2017, U.S. Pat. No. 10,405,971.

U.S. Appl. No. 16/550,144, filed Aug. 23, 2019, US 20200113674A1.

U.S. Appl. No. 12/602,454, filed Dec. 15, 2009, U.S. Pat. No. 8,475,528.

U.S. Appl. No. 13/244,452, filed Sep. 24, 2011, U.S. Pat. No. 8,535,375.

U.S. Appl. No. 12/667,510, filed Dec. 31, 2009, U.S. Pat. No. 9,114,006.

U.S. Appl. No. 14/812,104, filed Jul. 29, 2015, U.S. Pat. No. 9,907,647.

U.S. Appl. No. 12/995,263, filed Dec. 15, 2010, U.S. Pat. No. 9,554,894.

U.S. Appl. No. 15/382,377, filed Dec. 16, 2016, U.S. Pat. No. 10,517,717.

U.S. Appl. No. 12/997,651, filed Dec. 13, 2010, U.S. Pat. No. 8,382,769.

(56) References Cited

OTHER PUBLICATIONS

U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.
U.S. Appl. No. 15/071,880, filed Mar. 16, 2016, U.S. Pat. No. 10,039,668.
U.S. Appl. No. 15/336,678, filed Oct. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 16, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,364,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.
U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, U.S. Pat. No. 10,383,723.
U.S. Appl. No. 15/756,565, filed Feb. 28, 2018, U.S. Pat. No. 10,849,738.
U.S. Appl. No. 15/756,569, filed Feb. 28, 2018, U.S. Pat. No. 10,799,339.
U.S. Appl. No. 16/313,180, filed Dec. 26, 2018, US 20190192284A1.
U.S. Appl. No. 16/313,184, filed Dec. 26, 2018, US 20190151078A1.

* cited by examiner

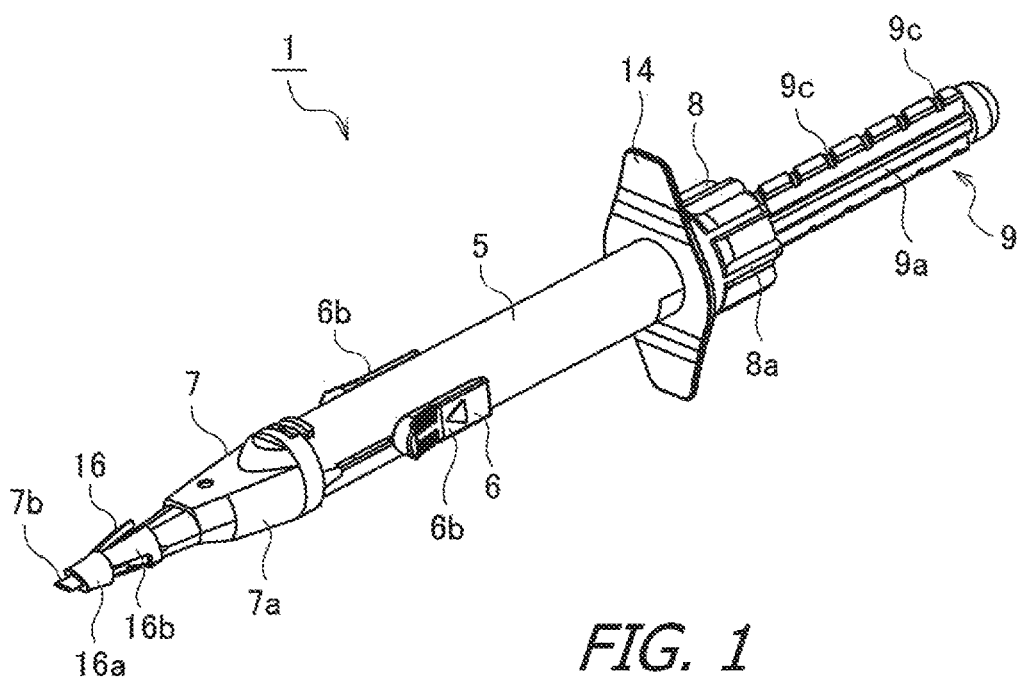
FIG. 1
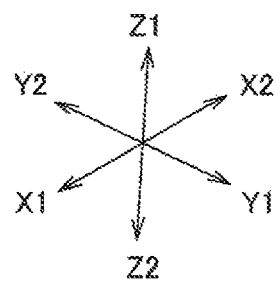

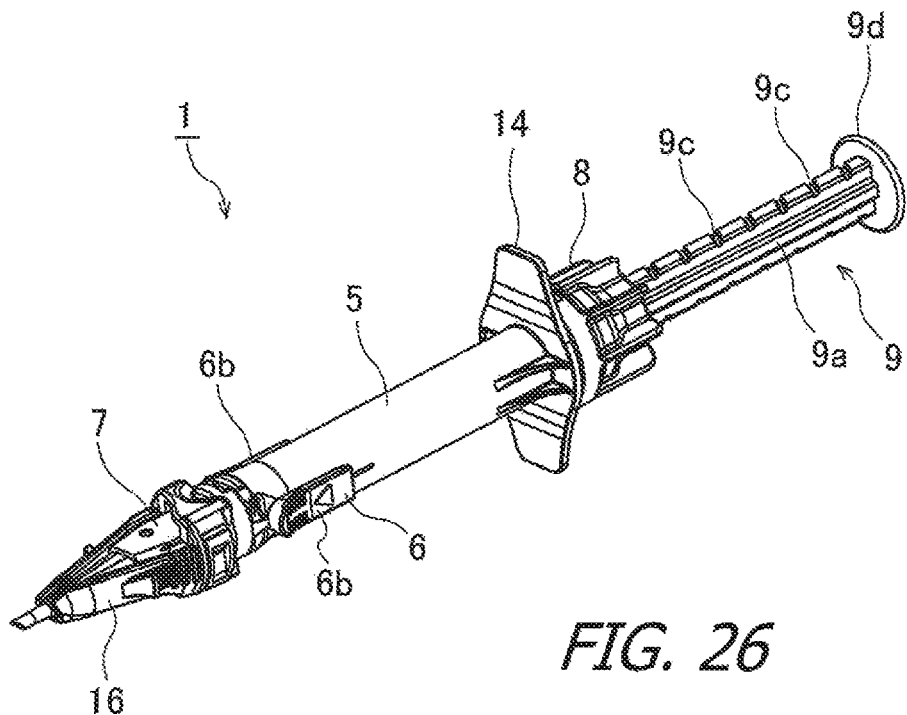
FIG. 26
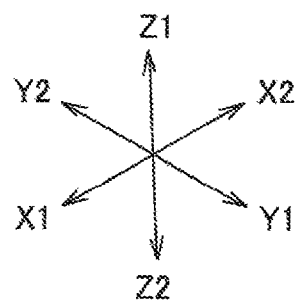

INTRAOCULAR LENS INJECTOR

TECHNICAL FIELD

The present invention relates to an intraocular lens injector used for injecting an intraocular lens into an eyeball (intraocular).

DESCRIPTION OF RELATED ART

Cataract surgery involves the removal of a cloudy crystalline lens by ultrasonic emulsification followed by implantation on an intraocular lens into an eye. Currently, an intraocular lens made of a soft material such as silicone elastomer is used and is injected into an eye using an intraocular lens injector.

The intraocular lens injector described in Patent Document 1 has a configuration in which a plunger meshes with a screw member by screw mechanism and moves in an axial direction of an injector main body by rotating a rotary member coupled to the injector main body. The plunger is coupled to a rod which pushes the intraocular lens out of the injector main body. In the explanation hereafter, a system of pushing out an intraocular lens by a rotational operation of the rotary member or the like is called a screw system.

Meanwhile, the intraocular lens injector described in Patent Document 2 has a configuration in which the plunger moves in the axial direction of the injector main body by pushing the plunger against the injector main body. The plunger is coupled to a rod which pushes the intraocular lens out of the injector main body. In the explanation hereafter, a system of pushing out the intraocular lens by pushing operation of a plunger or the like is called a push system.

PRIOR ART DOCUMENT

Patent Document

[Patent Document 1] Japanese Unexamined Patent Publication No. 2015-177845
[Patent Document 2] Japanese Unexamined Patent Publication No. 2016-87336
[Patent Document 3] Japanese Unexamined Patent Publication No. 2003-210498

SUMMARY OF THE INVENTION

Problem to be Solved by the Invention

The above-described screw and push systems have different usability. For example, the screw system has an advantage in that it is easy to control the speed and force of the rod when pushing out the intraocular lens, because the rod moves according to a rotation of the rotary member. On the other hand, the push system has an advantage in that a user can operate the plunger with just one hand, leaving the spare hand for other necessary purposes (for example, to hold an eyeball). Among all users of intraocular lens injectors (surgeon such as an ophthalmologist), some may prefer the screw system while others prefer the push system, when performing cataract surgery. Accordingly, in order to cater to the preferences of both types of users, it is necessary for an intraocular lens injector to have both push and screw systems.

Patent Document 3 discloses an intraocular lens injector including an injector main body, a pushing shaft, and a screw cylinder. In this intraocular lens injector, a male thread is formed on the injector main body and a female thread is formed on the pushing shaft. When the screw cylinder is rotated, the pushing shaft moves by meshing (screwing) between the male screw and the female screw. The pushing shaft will also move even when the end portion of the pushing shaft is pressed (pushed in).

However, the intraocular lens injector described in Patent Document 3 has the following points to be improved. Namely, the screw cylinder is attached near the end of the pushing shaft so as to rotate independently of the pushing shaft, and in an initial state before use, the injector main body and the screw cylinder are disposed apart from each other in the axial direction of the pushing shaft. Therefore, when pushing in the pushing shaft to operate by the push system, the male thread of the injector main body and the female thread of the screw cylinder come into contact (collide) with each other during operation. Then, at the moment when the male screw and the female screw come into contact with each other, a vibration or an impact is generated in the intraocular lens injector, and this may cause the position of the intraocular lens inside the injector body to deviate from its normal position. Further, in order to operate by the screw system, it is necessary to temporarily push the end portion of the pushing shaft forward and make the male screw and the female screw mesh with each other, in other words, it is necessary to perform a pushing operation as well. Namely, the intraocular lens injector described in Patent Document 3 employs a system in which both the pushing operation of the pushing shaft and the rotational operation of the screw cylinder are required. It is not possible to push out the intraocular lens only by rotational operation.

A main object of the present invention is to provide an intraocular lens injector capable of responding to both the push system and the screw system, does not cause or minimize vibration or the like and can be used to inject an intraocular lens only by rotational operation (screw system).

Means for Solving the Problem (First Aspect)
A first aspect of the present invention is an intraocular lens injector for injecting an intraocular lens into an eye, including:
a hollow body having a lens installing portion on which an intraocular lens is installed;
a rotary member having a first threaded portion formed thereon, and attached to a rear end portion of the hollow body, rotatably around an axis of the hollow body;
a plunger having a second threaded portion formed thereon, and configured to move through the hollow body in an axial direction of the hollow body; and
a pushing member configured to push out an intraocular lens from the lens installing portion by moving through the hollow body in the axial direction of the hollow body together with the plunger,
wherein a tip side of the plunger is inserted into the hollow body in a state in which the first threaded portion and the second threaded portion are meshed with each other, and a rear end side of the plunger is disposed in a state of protruding backward of the rotary member.
(A Second Aspect)
A second aspect of the present invention is the intraocular lens injector of the first aspect, wherein the hollow member has a rotation restricting portion for restricting a rotation of the plunger.

(Third Aspect)

A third aspect of the present invention is the intraocular lens injector of the first aspect or the second aspect, wherein the hollow body has an anti-falloff portion for preventing the plunger from falling off from the hollow body.

(Fourth Aspect)

A fourth aspect of the present invention is the intraocular lens injector of any one of the first to third aspects, wherein a taper angle of a rear side of the second threaded portion is 5° or more and 15° or less.

(Fifth Aspect)

A fifth aspect of the present invention is the intraocular lens injector of the second aspect, wherein the rotation restricting portion is provided rotatably so as to open and close an opening formed on an outer wall of the hollow body, and at least a part of the rotation restricting portion is shielded by the rotary member.

(Sixth Aspect)

A sixth aspect of the present invention is the intraocular lens injector of any one of the first to fifth aspects, wherein a pressing plate portion is provided at the rear end portion of the plunger.

(Seventh Aspect)

A seventh aspect of the present invention is the intraocular lens injector of any one of the first to sixth aspects, wherein an intraocular lens is installed on the lens installing portion.

Advantage of the Invention

According to the present invention, there is provided an intraocular lens injector capable of responding to both of a push system and a screw system, does not cause or minimizes vibration or the like and can be used to inject an intraocular lens only by rotational operation (screw system).

BRIEF DESCRIPTION OF THE DRAWING

FIG. 1 is a perspective view showing a configuration example of an intraocular lens injector according to a first embodiment of the present invention.

FIGS. 7A to 7C show the configuration of an injection tube, wherein FIG. 7A is a plan view, FIG. 7B is a side view, and FIG. 7C is a bottom view.

FIGS. 10A to 10C show a configuration of an attachment member, wherein FIG. 10A is a plan view, FIG. 10B is a side view, and FIG. 10C is a rear view.

FIG. 11 shows a state in which an attachment member is attached to the injection tube, wherein

FIGS. 12A to 12C show a preferable embodiment when the attachment member is used, wherein FIG. 12A is a cross-sectional view as seen from the axial direction, and FIG. 12B is a cross-sectional view as seen from a direction orthogonal to the axial direction.

FIGS. 22A to 22D show the configuration of the attachment member according to the second embodiment of the present invention, wherein FIG. 22A is a plan view, FIG. 22B is a side view, FIG. 22C is a bottom view, and FIG. 22D is a rear view.

FIGS. 23A to 23C show a state in which the attachment member is attached to the injection tube, wherein FIG. 23A is a plan view, FIG. 23B is a side view, and FIG. 23C is a bottom view.

FIG. 26 is a perspective view showing a configuration of the intraocular lens injector according to a third embodiment of the present invention.

FIG. 27A is a plan view showing a configuration of the intraocular lens injector according to a third embodiment of the present invention, wherein

FIGS. 28A to 28C are perspective views showing a configuration of the injector main body according to the third embodiment of the present invention, FIG. 28A shows a state in which the rotation restricting portion provided in the injector main body is opened, and FIG. 28B shows a state in which the rotation restricting portion is closed.

FIGS. 29A to 29C show a configuration of the injection tube according to a third embodiment of the present invention, wherein FIG. 29A is a plan view, FIG. 29B is a side view, and FIG. 29C is a bottom view.

FIGS. 31A and 31B are perspective views of the attachment member according to the third embodiment of the present invention as seen obliquely from above, wherein FIG. 31A shows the attachment member before being attached to the injection tube, and FIG. 31B shows the attachment member after being attached to the injection tube.

FIGS. 32A to 32C show a configuration of the attachment member according to the third embodiment of the present invention, wherein FIG. 32A is a plan view, FIG. 32B is a side view, and FIG. 32C is a bottom view.

DETAILED DESCRIPTION OF THE INVENTION

Figure 2A:
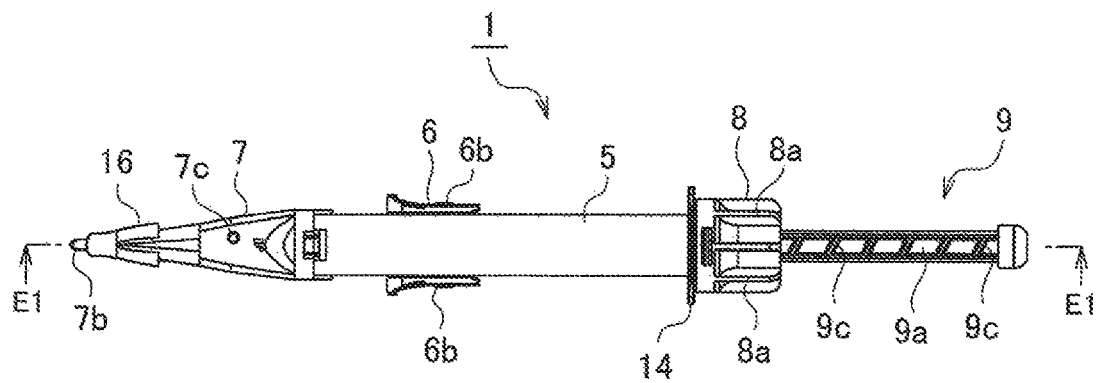
FIG. 2A is a plan view showing a configuration example of the intraocular lens injector according to the first embodiment of the present invention.
Figure 2B:
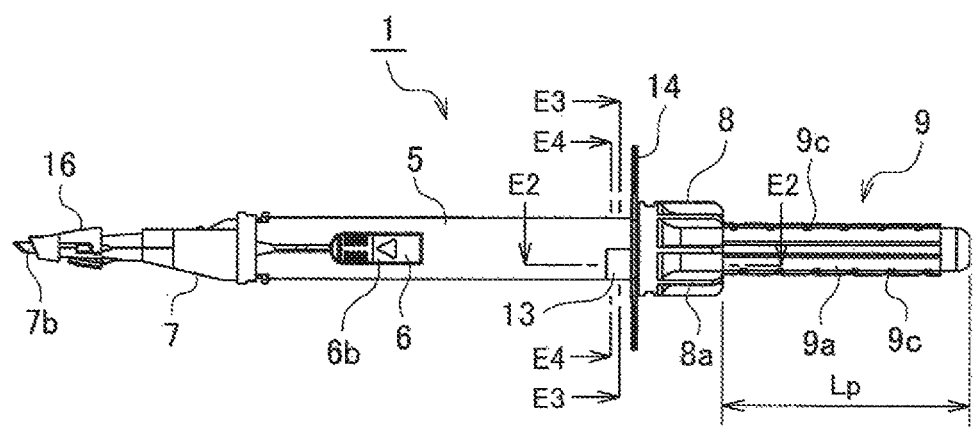
FIG. 2B is a side view.
Figure 2C:
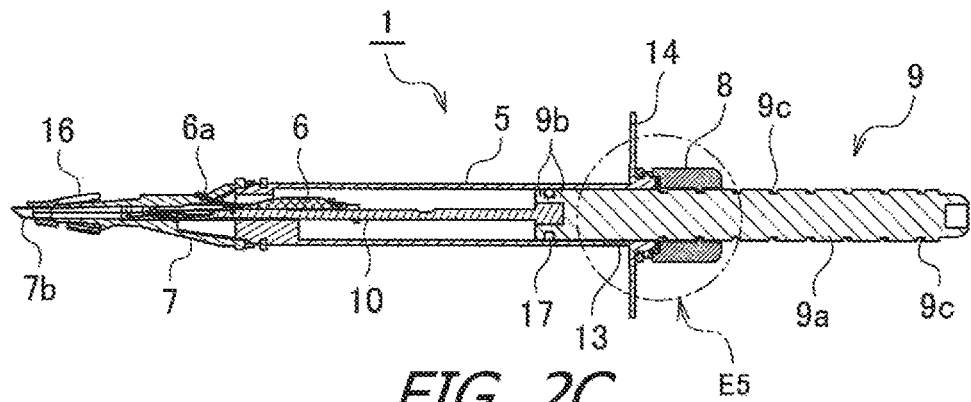
FIG. 2C is a sectional view taken along the line E1-E1.

Embodiments of the present invention will be described hereafter, with reference to the drawings.
<Configuration of the Intraocular Lens Injector>
FIG. 1 is a perspective view showing a configuration example of an intraocular lens injector according to a first embodiment of the present invention. Further, FIG. 2A is a plan view showing a configuration example of the intraocular lens injector according to the first embodiment of the present invention, FIG. 2B is a side view, FIG. 2C is a cross-sectional view taken along the line E1-E1.

An intraocular lens injector 1 is used for injecting an intraocular lens into an eye. In this embodiment, as an example of the intraocular lens, there is provided an intraocular lens 4 as a one-piece type intraocular lens 4 (see FIG. 6) made of a soft material such as silicone elastomer or soft acrylic, including a circular optical portion 4a which performs an optical function and two supporting portions 4b that curve outward from two positions on the outer circumferential portion of the optical portion 4a and extend outward.

Further, in this embodiment, in describing a relative positional relationship and a direction of movement and the like of each part of the intraocular lens injector 1, one of the X axis directions is defined as X1 direction, the other direction is defined as X2 direction, and one of the Y axis directions is defined as Y1 direction, the other direction is defined as Y2 direction, and one of the Z axis directions is defined as Z1 direction and the other direction is defined as Z2 direction, and X1 direction is defined as a front side (frontward), X2 direction is defined as a rear end side (rearward), Y1 direction is defined as a left side (leftward), and Y2 direction is defined as a right side (rightward), Z1 direction is defined as an upper side (upward), and Z2 direction is defined as a downside (downward). Among them, the X axis direction (X1 direction and X2 direction) corresponds to a length direction of the intraocular lens injector 1, and the Y axis direction (Y1 direction and Y2 direction) corresponds to a width direction of the intraocular lens injector 1, and the Z axis direction (Z1 direction and Z2 direction) corresponds to a height direction of the intraocular lens injector 1.

The intraocular lens injector 1 has a configuration including an injector main body 5, a slider 6, an injection tube 7, a rotary member 8, a plunger 9, a rod 10 (see FIG. 2C), and an attachment member 16. These constituent elements are preferably constituted by resin molded products, respectively. The injector main body 5 and the injection tube 7 have a hollow structure and are coupled to each other to thereby constitute a hollow body. The slider 6 is attached to the injector main body 5. The injection tube 7 is coupled to the tip part of the injector main body 5. The rotary member 8 is rotatably connected to a rear end portion of the injector main body 5. The plunger 9 is disposed coaxially with the injector main body 5. A part of the plunger 9 is disposed inside of the injector main body 5 through the rotary member 8, and the other part of the plunger 9 is disposed to protrude rearward from the rotary member 8. The rod 10 is disposed inside of the hollow body which is composed of the injector main body 5 and the injection tube 7. The attachment member 16 is a member attached to the hollow body so as to provide a predetermined additional function.

Figure 3:
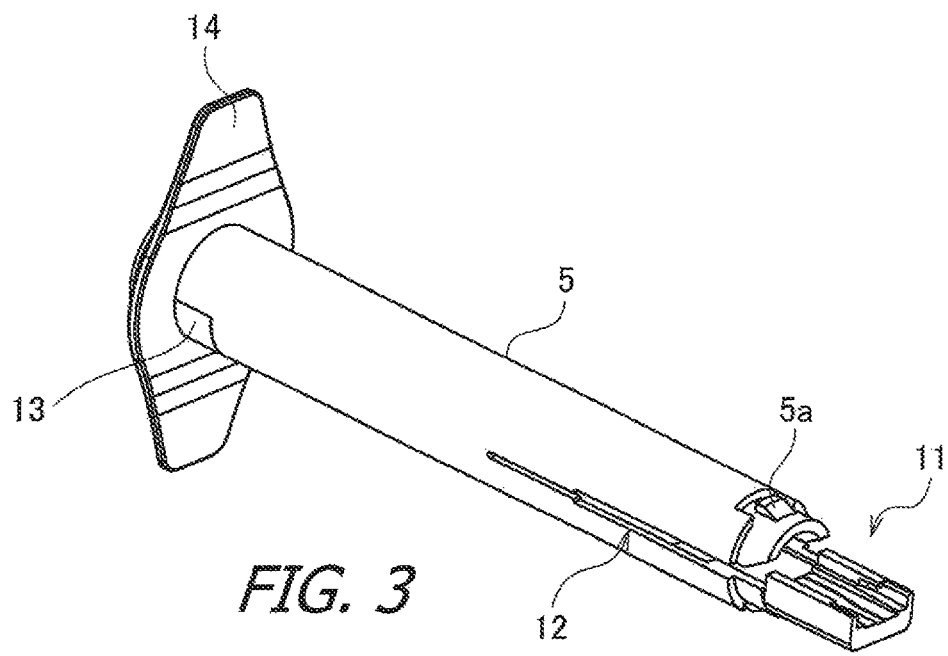
FIG. 3 is a perspective view showing a configuration of an injector main body.
Figure 4A:
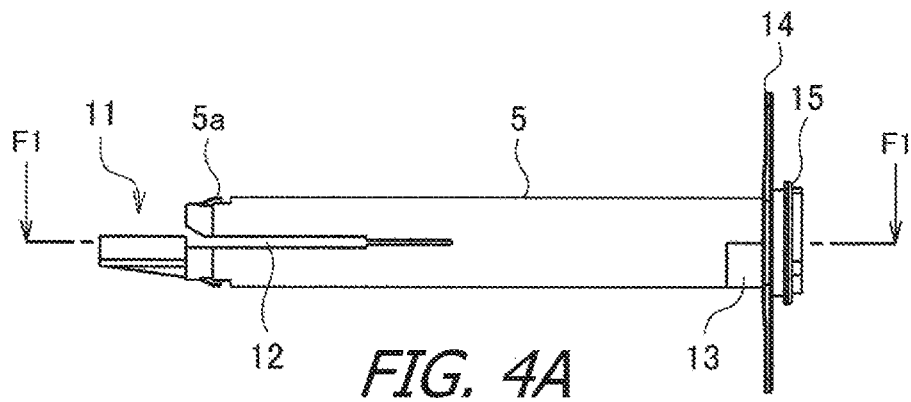
FIG. 4A is a side view showing a configuration of an injector main body.
Figure 4B:
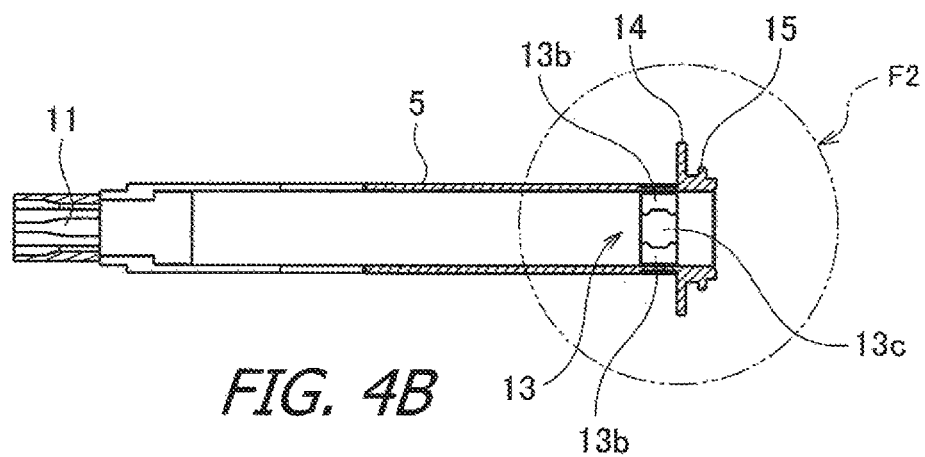
FIG. 4B is a sectional view taken along the line F1-F1 in FIG. 4A.
Figure 4C:
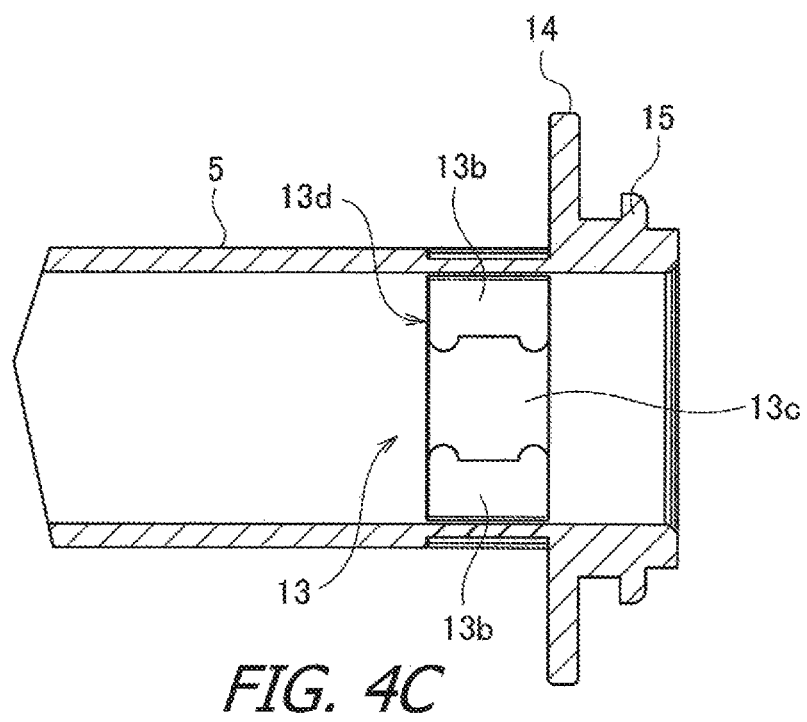
FIG. 4C is an enlarged view of a portion F2 in FIG. 4B.

(Injector Main Body)
FIG. 3 is a perspective view showing the configuration of the injector main body. Further, FIG. 4A is a side view showing a configuration of an injector main body, FIG. 4B is a cross-sectional view taken along the line F1-F1 in FIG. 4A, and FIG. 4C is an enlarged view of a portion F2 in FIG. 4B.

The injector main body 5 is formed in a cylindrical shape as a whole. A lens installing portion 11 is provided at the tip part of the injector main body 5. The intraocular lens 4 is installed on the lens installing portion 11. The lens installing portion 11 is formed so as to protrude forward from an outer circumferential wall on a lower side of the injector main body 5.

An injection tube coupling portion 5a is formed on the outer circumferential portion on the tip side of the injector main body 5. Slits 12 are respectively formed on both left and right sides of the injector main body 5. The slits 12 are formed on the tip side of the injector main body 5. When the slider 6 is attached to the injector main body 5, the slits 12 movably support the slider 6 in the axial direction (central axis direction) of the injector main body 5.

The rear end of the injector main body 5 opens in a circular shape, through which the plunger 9 and the rod 10 can be inserted into the injector main body 5. A rotation restricting portion 13, a flange portion 14, and a rotation supporting portion 15 are formed at the rear end portion of the injector main body 5 and in the vicinity thereof. The rotation restricting portion 13 restricts a rotation of the plunger 9 inserted into the injector main body 5.

Figure 5A:
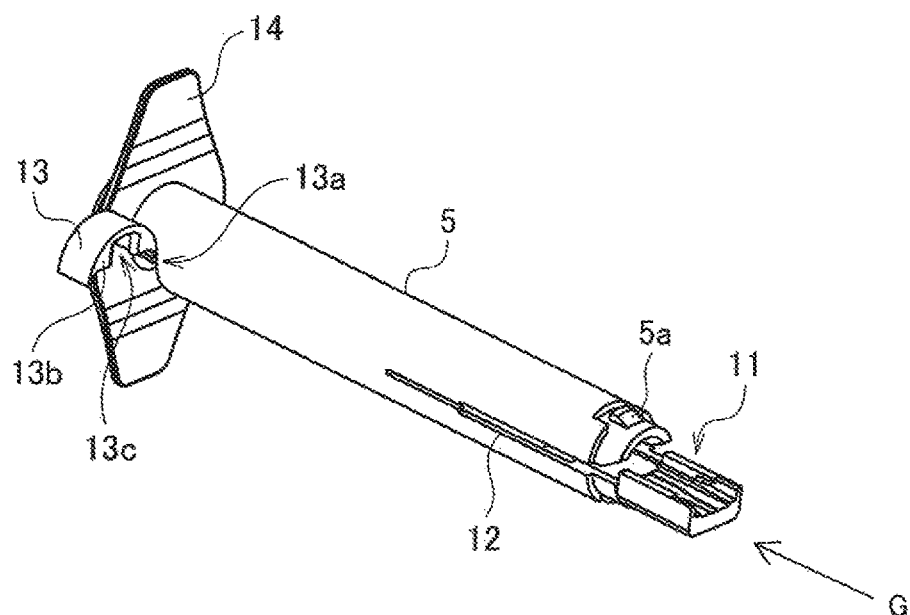
FIG. 5A is a perspective view showing an injector main body in a state in which a rotation restricting part is opened.
Figure 5B:
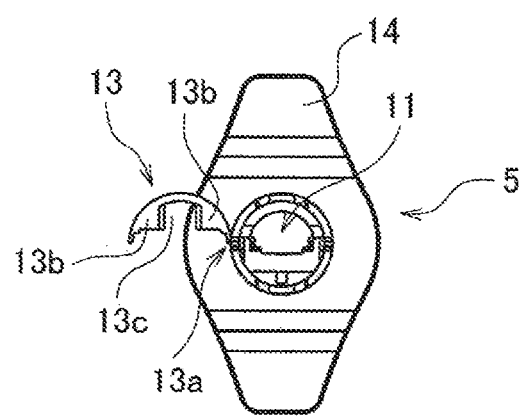
FIG. 5B is a view seen from arrow G in FIG. 5A.

FIGS. 4A to 4C show the injector main body in a state in which the rotation restricting portion is closed. In contrast, FIG. 5A is a perspective view showing the injector main body in a state in which the rotation restricting portion is opened, and FIG. 5B is a view seen from arrow G in FIG. 5A.

The rotation restricting portion 13 is formed slightly forward of the flange portion 14. The rotation restricting portion 13 constitutes a part of an outer circumferential wall of the injector main body 5, and is provided so as to be rotatable around a pivotally supporting portion 13a so as to open and close an opening formed on the outer circumferential wall. Further, a pair of sliding guides 13b is formed in the rotation restricting portion 13, and a recessed guide groove 13c is formed between these sliding guides 13b. The pair of sliding guides 13b is disposed in a tube of the injector main body 5 when the rotation restricting portion 13 is closed, and is disposed outside of the tube of the injector main body 5 when the rotation restricting portion 13 is opened. A closed state of the rotation restricting portion 13 is maintained, for example, by an engagement of recessed and protruded portions (not shown). When the rotation restricting portion 13 is rotated around the pivotally supporting portion 13a against a holding force caused by the engagement of the recessed and protruded portions, as shown in FIG. 5, the rotation restricting portion 13 is opened. Tip surfaces of the respective sliding guides 13b are formed as anti-falloff portions 13d (see FIG. 4C). The anti-falloff portions 13d prevent the plunger 9 from being pulled out from the injector main body 5.

The flange portion 14 is a portion for hooking a finger (usually an index finger and a middle finger) of a user's hand, when operating the intraocular lens injector 1 by a push system. The rotation supporting portion 15 is provided slightly rearward of the flange portion 14. The rotation supporting portion 15 is formed in a ring shape having a stepped structure protruding in a ring shape.

Figure 6:
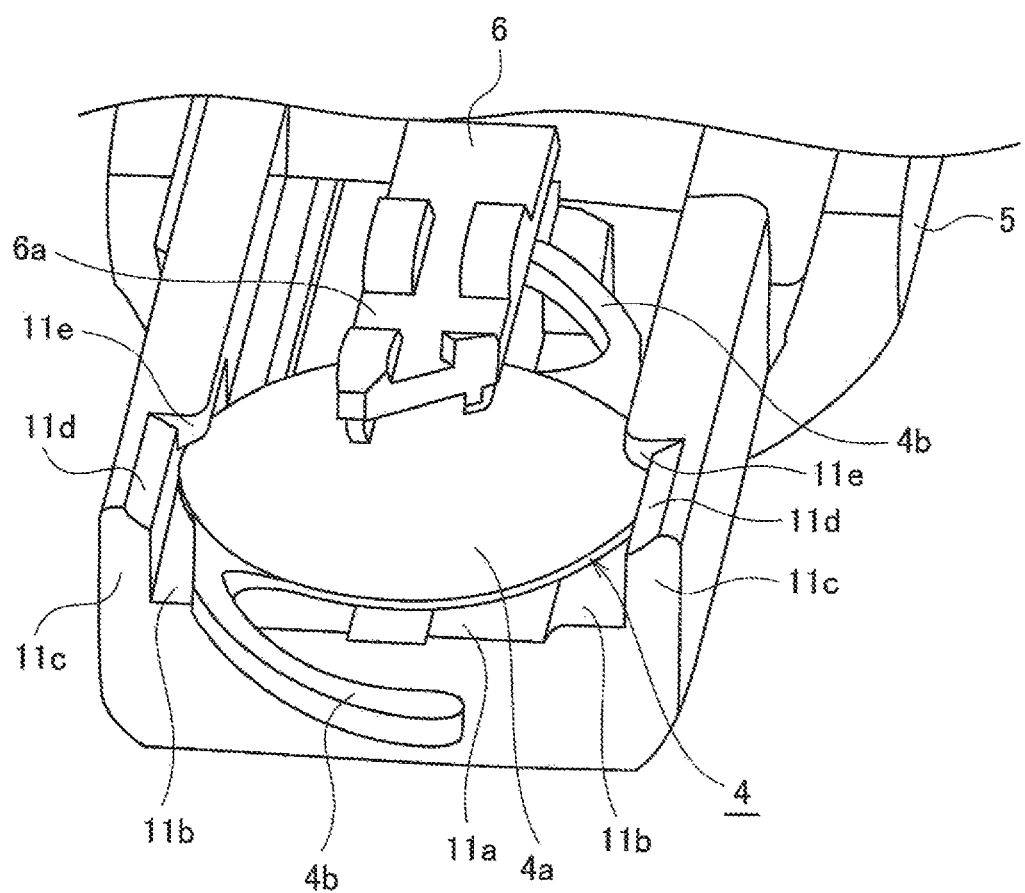
FIG. 6 is a perspective view showing a configuration and an arrangement of a tip part of the injector main body.

As shown in FIG. 6, the lens installing portion 11 includes a bottom surface portion 11a, a lens receiving portion 11b, and a lens guide portion 11c. The lens receiving portion 11b receives and supports the intraocular lens 4 from below. The intraocular lens 4 is installed on the lens installing portion 11 in a state in which one supporting portion 4b is disposed in front and the other supporting portion 4b is disposed in rear. The intraocular lens injector 1 is of a preload type in which the intraocular lens 4 is previously installed on the lens installing portion 11 of the injector main body 5. Therefore, the intraocular lens 4 is one of the components of the intraocular lens injector 1. However, in executing the present invention, the intraocular lens injector 1 is not necessarily required to be the preload type.

A center portion in a width direction of the bottom surface portion 11a is slightly recessed. The lens receiving portion 11b is formed on both left and right sides of the lens installing portion 11. The lens receiving portion 11b is formed to be one step higher than the bottom surface portion 11a. This is because when the intraocular lens 4 is supported on the lens receiving portion 11b, the optical portion 4a of the intraocular lens 4 is supported in a floating state from the bottom surface portion 11a without contacting the bottom surface portion 11a. In the same manner as in the lens receiving portion 11b, the lens guide portion 11c is formed on both right and left sides of the lens installing portion 11. The lens guide portion 11c guides the optical portion 4a of the intraocular lens 4 supported by the lens receiving portion 11b so as to sandwich the optical portion 4a from both the left and right sides. The lens guide portion 11c is formed in a vertically upright state from the lens receiving portion 11b. On upper end portions of the left and right lens guide portions 11c, an inclined surface 11d and a restricting portion 11e are formed adjacent to each other in the axial direction of the injector main body 5. The inclined surface 11d is formed so as to incline outwardly to easily receive the intraocular lens 4 on the lens installing portion 11. The inclined surface 11d is formed on the tip side of the lens installing portion 11 with respect to the restricting portion 11e in the axial direction of the injector main body 5. The restricting portion 11e is formed to protrude toward the center in the width direction of the lens installing portion 11. The restricting portion 11e limits a movable range in a vertical direction of the intraocular lens 4 which is supported by the lens receiving portion 11b.

(Slider)

As shown in FIG. 1, FIG. 2A, FIG. 2B, and FIG. 6, the slider 6 has a configuration including a lens pressing portion 6a and a pair of wing portions 6b. The lens pressing portion 6a is disposed at the tip part of the slider 6, and the pair of wing portions 6b is disposed in pairs on the left and right sides of the slider 6. When the slider 6 is moved forward, as shown in FIG. 6, the lens pressing portion 6a is disposed so as to advance to the upper side of the optical portion 4a of the intraocular lens 4 which is installed on the lens installing portion 11.

The pair of wing portions 6b is disposed outside of the outer circumferential wall portion of the injector main body 5. The pair of wing portions 6b is the portions with which a user's finger (usually an index finger and thumb) is brought into contact, when the slider 6 is moved in the axial direction of the injector main body 5 during use of the intraocular lens injector 1. The user is a surgeon such as an ophthalmologist performing surgery or a nurse assisting a surgeon. On the outer surface of each wing portion 6b, unevenness for anti-falloff and a mark (triangular arrow in this embodiment) indicating the moving direction of the slider 6 are formed. Further, the outer surface of each wing portion 6b is curved from the rear end side toward the tip side so that the fingers of the user are easily caught, and unevenness for anti-falloff is formed on this curved portion.

(Injection Tube)

Figure 7A:
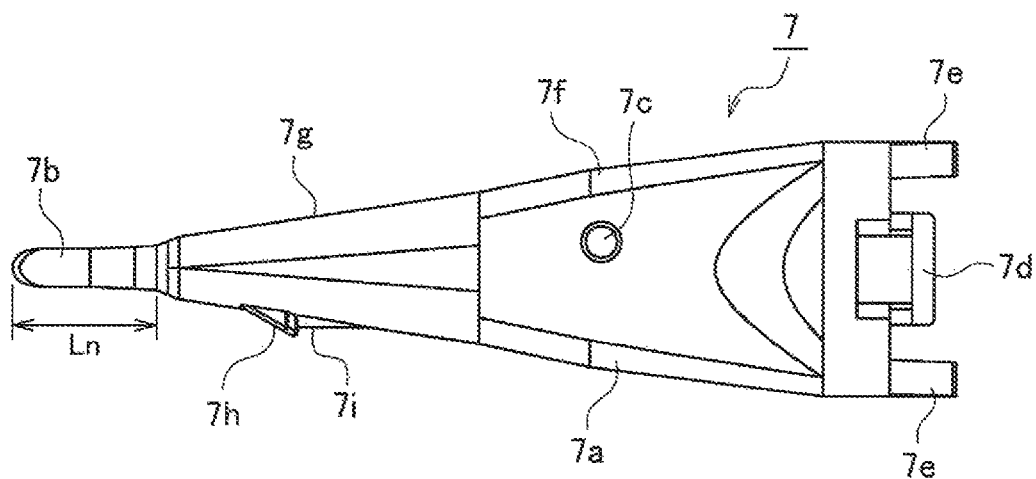
Figure 7B:
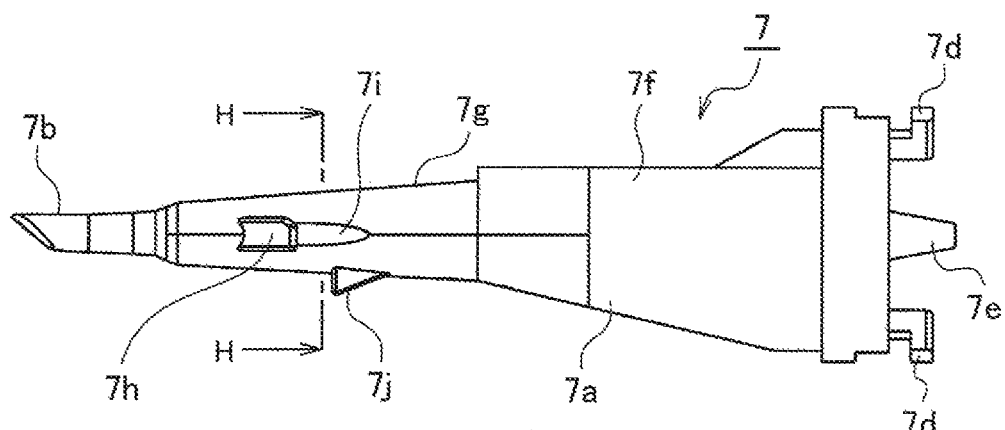
Figure 7C:
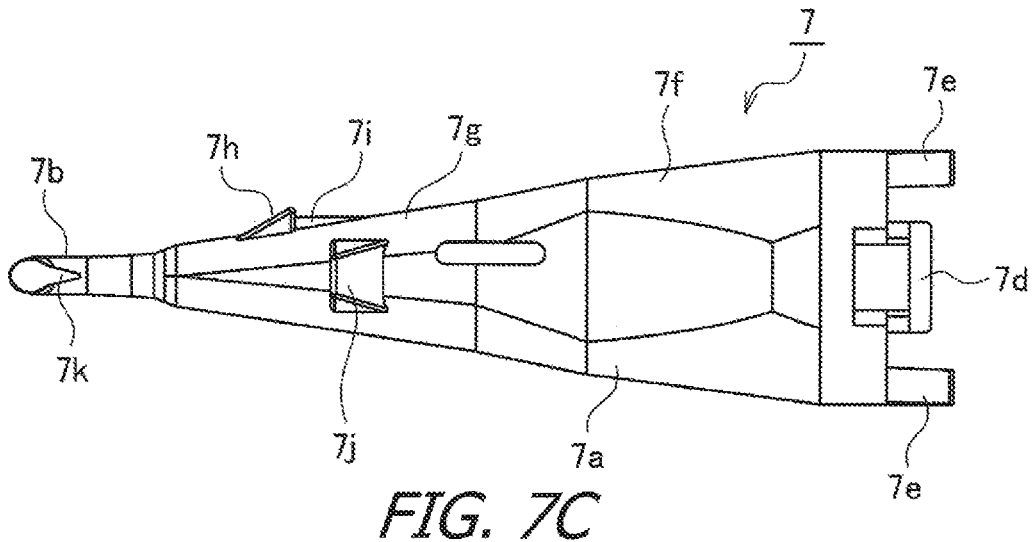
Figure 8:
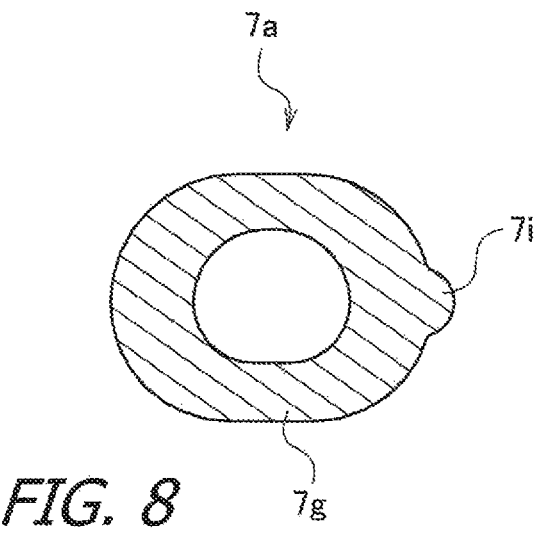
FIG. 8 is a cross-sectional view taken along the line H-H in FIG. 7B.

FIGS. 7A to 7C show the configuration of an injection tube, wherein FIG. 7A is a plan view, FIG. 7B is a side view, and FIG. 7C is a bottom view. Further, FIG. 8 is a cross-sectional view taken along the line H-H in FIG. 7B.

The injection tube 7 is a tube for folding the intraocular lens 4 small and guiding it into the eye, when the intraocular lens 4 installed on the lens installing portion 11 is injected into the eye. The injection tube 7 is made of a transparent or translucent material, so that a state of the intraocular lens 4 moving inside of the insertion tube 7 can be visually recognized from the outside.

The injection tube 7 has a hollow injection tube main body 7a and a narrow tubular nozzle portion 7b. The injection tube 7 is attached to the tip part of the injection main body 5. At this time, the lens installing portion 11 of the injector main body 5 is housed and disposed inside of the injector main body 7a of the injection tube 7, together with the intraocular lens 4 installed thereon. An injection hole 7c is formed on an upper surface of the injection tube main body 7a. The injection hole 7c is a hole through which a viscoelastic substance (for example, sodium hyaluronate etc.) is injected. The viscoelastic substance injected from the injection hole 7c is supplied to the intraocular lens 4 installed on the lens installing portion 11.

Meanwhile, the rear end portion of the injection tube main body 7a is opened, and hooking portions 7d and wedge portions 7e are formed around the opening portion. The hooking portions 7d are disposed in pairs at the top and bottom, and the wedge portions 7e are disposed in pairs on the right and left. The hooking portions 7d are portions to be hooked on the injection tube coupling portion 5a of the injector main body 5 when the injection tube 7 is attached to the tip part of the injector main body 5. The wedge portions 7e are portions to be inserted into an entrance portion of the slit 12 of the injector main body 5 when the injection tube 7 is attached to the injector main body 5.

The injection tube main body 7a is divided into a first portion 7f and a second portion 7g in the axial direction of the injection tube 7. The first portion 7f has an internal space capable of housing the lens installing portion 11 of the injector main body 5, and is formed wider than the second portion 7g. The second portion 7g is located forward of the first portion 7f. The internal space of the injector main body 7a is gradually narrowed from the first portion 7f to the second portion 7g in order to fold the intraocular lens 4 small when the intraocular lens 4 is pushed out by the rod 10.

A first protrusion 7h, a second protrusion 7i, and a third protrusion 7j are formed on the second portion 7g of the injection tube main body 7a. These three protrusions 7h, 7i, and 7j are formed as engaged portions, correspondingly to an engaging portion 16b described later, in order to make an engagement between the attachment member 16 and the injection tube 7. The first protrusion 7h is formed in a state of protruding from one side (left side) surface of the second portion 7g. The second protrusion 7i is formed in a state adjacent to and behind the first protrusion 7h. The second protrusion 7i protrudes from one side (left side) surface of the second protrusion 7i with a protrusion amount smaller than that of the first protrusion 7h. The third protrusion 7j is formed to protrude downward from the lower surface of the second portion 7g. The third protrusion 7j is formed displaced rearward from the first protrusion 7h.

The nozzle portion 7b is a portion to be inserted into the incisional wound of the eyeball, when the intraocular lens 4 is injected into the eye using the intraocular lens injector 1. The nozzle portion 7b is formed at the tip part of the injection tube 7. The nozzle portion 7b is formed so as to protrude forward from the tip of the second portion 7g of the injection tube main body 7a. The nozzle portion 7b is formed in a substantially circular shape when viewed from the axial direction of the injection tube 7. An outer circumferential diameter of the nozzle portion 7b is substantially uniform over an entire length Ln of the nozzle portion 7b. The tip part of the nozzle portion 7b opens with an oblique incisional wound from the top to the bottom, through which the intraocular lens 4 is released to the outside. A cutout portion 7k is formed in an opening edge on a lower side of the nozzle portion 7b. The cutout portion 7k is formed along the axial direction of the injection tube 7. The cutout portion 7k is preferably formed in a V shape as shown in the figure.

(Attachment Member)

Figure 9:
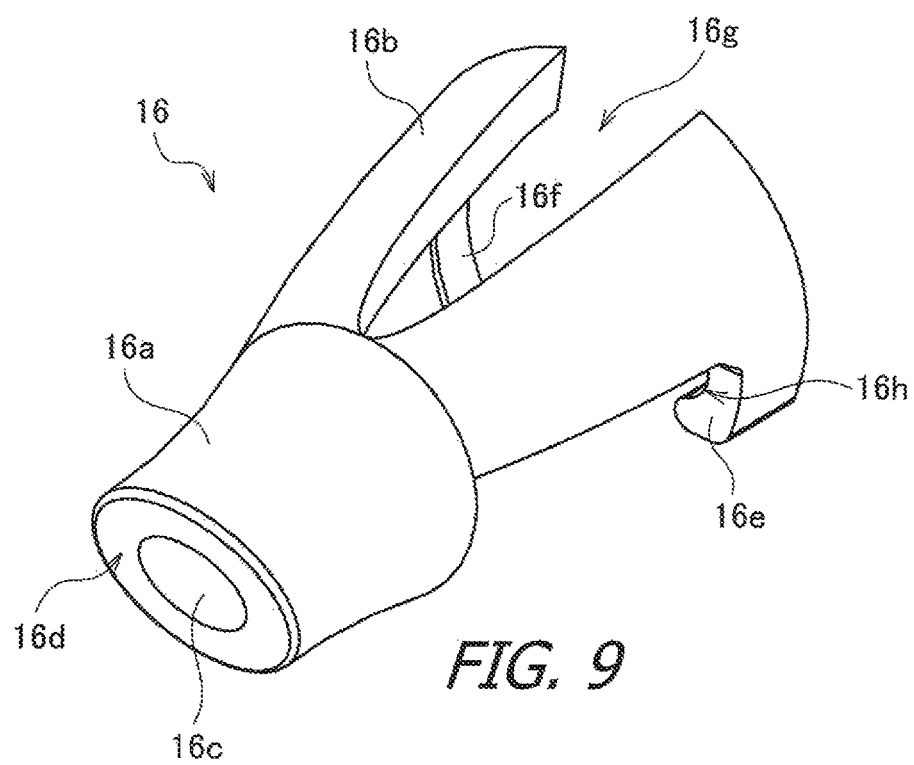
FIG. 9 is a perspective view showing a configuration of an attachment member.
Figure 10A:
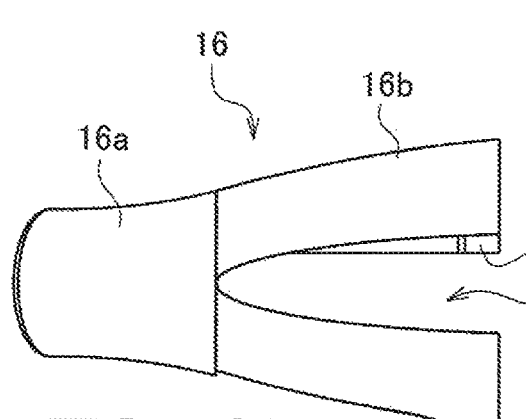
Figure 10C:
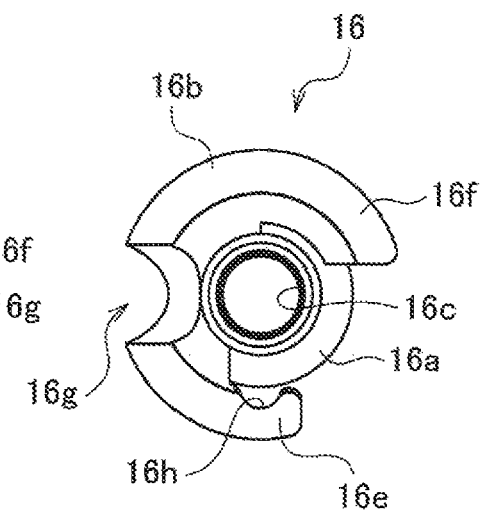
Figure 10B:
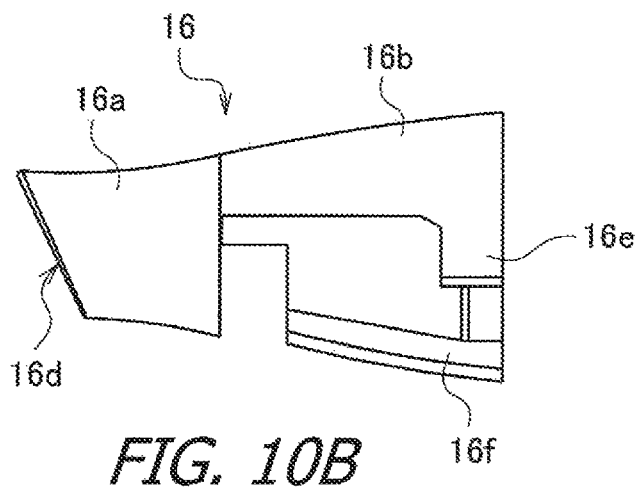

FIG. 9 is a perspective view showing a configuration of the attachment member. Further, FIGS. 10A to 10C a configuration of an attachment member, wherein FIG. 10A is a plan view, FIG. 10B is a side view, and FIG. 10C is a rear view.

As an example of the additional function described above, the attachment member 16 is a member that provides a function of limiting an injection amount of the nozzle portion 7b (hereinafter also referred to as "nozzle injection amount limiting function") when the nozzle portion 7b is inserted into the incisional wound of the eyeball. The nozzle injection amount limiting function is realized (details will be described later) using a tip surface 16d of the sleeve portion 16a of the attachment member 16.

The attachment member 16 is a member separate from the injection tube 7, and is configured to be movable with respect to the injection tube 7. A direction and a form of movement of the attachment member 16 with respect to the injection tube 7 are not particularly limited. For example, movement of the injection tube 7 in the axial direction, movement of the injection tube 7 in a direction intersecting (including orthogonal to) the axial direction of the injection tube 7, movement of the injection tube 7 in a direction around the axis, and movement of the injection tube 7 in a direction around the axis that intersects (including orthogonal to) the axial direction of the injection tube 7, and the like can be considered as the direction of the movement. Also, linear movement, rotational movement, twist movement, opening and closing (rocking) movement, expansion and contraction movement, and the like can be considered as the form of the movement. In this embodiment, the attachment member 16 is detachably attached to the injection tube 7 by the movement of the attachment member 16 with respect to the injection tube 7. "Detachably" described here means that "the attachment member 16 can be attached to the injection tube 7 and the attachment member 16 can be detached from injection tube 7". In the intraocular lens injector 1 of this embodiment, the attachment member 16 may be provided in a state of being attached to the injection tube 7 or in a state of being detached from the injection tube 7 in some cases. In each case, the attachment member 16 is one of the elements constituting the intraocular lens injector 1. Further, when using the nozzle injection amount limiting function provided by the attachment member 16, the attachment member 16 is attached to the injection tube 7, and when the function is not used, the attachment member 16 is detached from the injection tube 7. In the latter case, namely, even when the attachment member 16 is not used in the intraocular lens injection surgery, the attachment member 16 is still one of the elements constituting the intraocular lens injector 1.

The attachment member 16 includes a sleeve portion 16a and an engaging portion 16b. A through hole 16c is formed in the sleeve portion 16a, so that the nozzle portion 7b of the injection tube 7 can be engaged therewith. The through hole 16c is formed in a state penetrating the sleeve portion 16a in the axial direction. The tip surface 16d of the sleeve portion 16a is formed to be obliquely inclined with respect to the central axis of the sleeve portion 16a. The tip surface 16d of the sleeve portion 16a is disposed in a state of protruding outward (in a direction of enlarging the diameter) from the outer circumferential surface of the nozzle portion 7b when the attachment member 16 is attached to injection tube 7. This shows that the tip surface 16d of the sleeve portion 16a is a portion corresponding to the "protruding surface".

The shape of the protruding surface is not limited to an annular flat surface that is continuous in a circumferential direction like the tip surface 16d of the sleeve portion 16a, and may be formed in any form as long as it exhibits the nozzle injection amount limiting function. For example, the protruding surface may be discontinuously disposed in the circumferential direction by arrangement at least at one place in the circumferential direction, preferably two places, or three or more places at 180 degrees pitch. Also, the protruding surface may be a curved surface.

The engaging portion 16b is a portion to be engaged with the injection tube 7 when the attachment member 16 is attached to the injection tube 7. The engaging portion 16b is configured so that it can be engaged with the injection tube 7 and can release the engaged state, in order to make the attachment member 16 detachable from injection tube 7. The engaging portion 16b has a configuration in which a substantially trapezoidal conical outer circumferential wall corresponding to the outer circumferential shape of the injection tube main body 7a (second portion 7g) of the injection tube 7 is partially cut out. A hook portion 16e, a stopper portion 16f, and a viewing window 16g are formed in the engaging portion 16b. Among them, the hook portion 16e and the stopper portion 16f constitute a locking mechanism for temporarily positioning and fixing the attachment member 16 to the injection tube 7. The hook portion 16e is a portion to be hooked on the first protrusion 7h of the injection tube 7. On the inner circumferential side of the hook portion 16e, a semicircular recessed portion 16h is formed. The recessed portion 16h is configured to be able to engage and disengage with/from the second protrusion 7i of the injection tube 7 from the direction around the axis of the injection tube 7. "The direction around the axis" means a direction in which rotation is carried out around the central axis of a certain member. The stopper portion 16f is configured so that it can abut against the first protrusion 7h of the injection tube 7 from the direction around the axis of the injection tube 7, and so that it can abut against the third protrusion 7j of the injection tube 7 from the axial direction of the injection tube 7. The viewing window 16g is formed in a state in which the upper portion of the engaging portion 16b is cutout in a substantially V shape in plan view. The viewing window 16g is formed in order to allow a state of the intraocular lens 4 moving inside of the injection tube 7 to be visually recognized from the outside, even when the attachment member 16 is attached to the injection tube 7. A material of the attachment member 16 is not particularly limited, and for example, metal, ceramic, resin, and the like are used, and a transparent or translucent material is preferable so that the state of the intraocular lens moving inside of the injection tube 7 can be visually recognized from the outside. Further, the protruding surface of the attachment member 16 is in direct contact with a cornea when the intraocular lens is injected into the eye, thereby adding a load on the cornea, and therefore the attachment member 16 is preferably made of a soft resin such as silicone, urethane or the like in order to reduce the load.

Figure 11A:
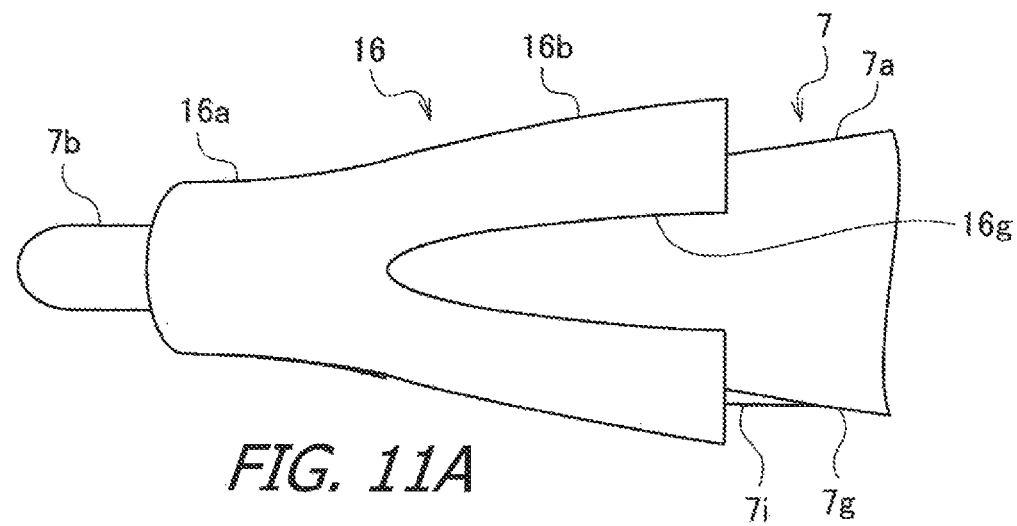
FIG. 11A is a plan view.
Figure 11B:
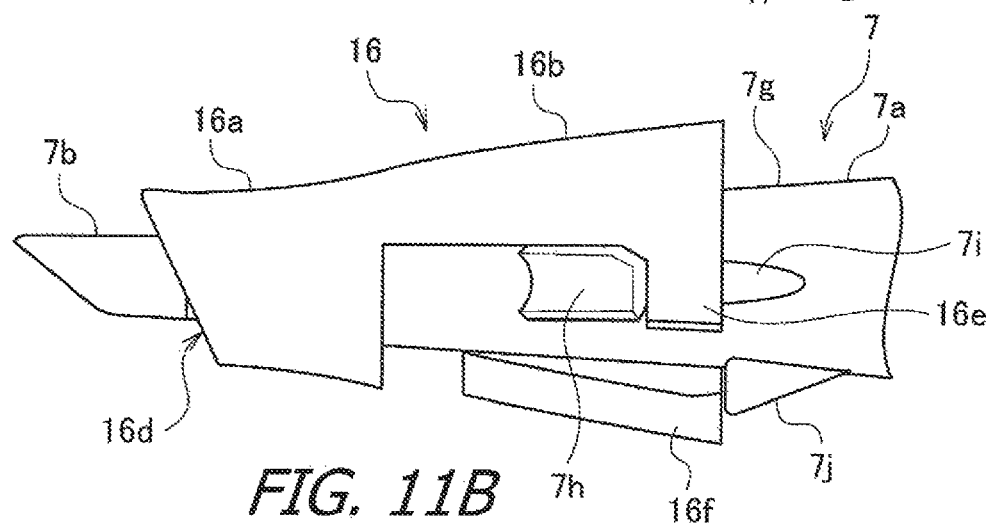
FIG. 11B is a side view.
Figure 11C:
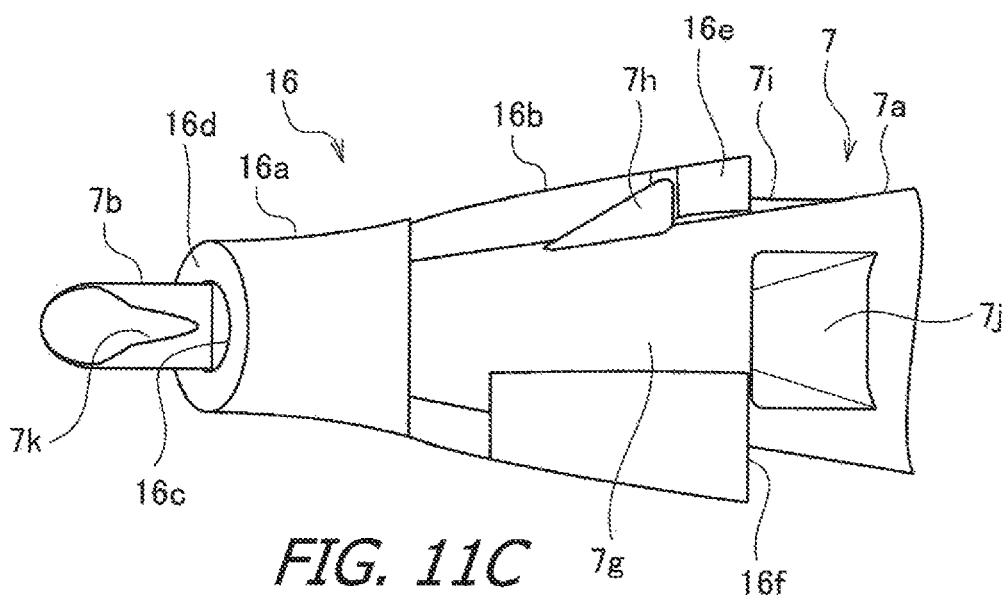
FIG. 11C is a bottom view.

FIGS. 11A to 11C show a state in which the attachment member is attached to the injection tube, wherein FIG. 11A is a plan view, FIG. 11B is a side view, and FIG. 11C is a bottom view.

As shown in the figure, in a state in which the attachment member 16 is attached to the injection tube 7, the nozzle portion 7b is engaged with the through hole 16c of the sleeve portion 16a. At this time, the tip surface 16d of the sleeve portion 16a is disposed in a state protruding outward from the outer circumferential surface of the nozzle portion 7b, and is disposed in a state inclined in the same direction as the cutout of the nozzle portion 7b with respect to the axial direction of the injection tube 7.

Figure 12A:
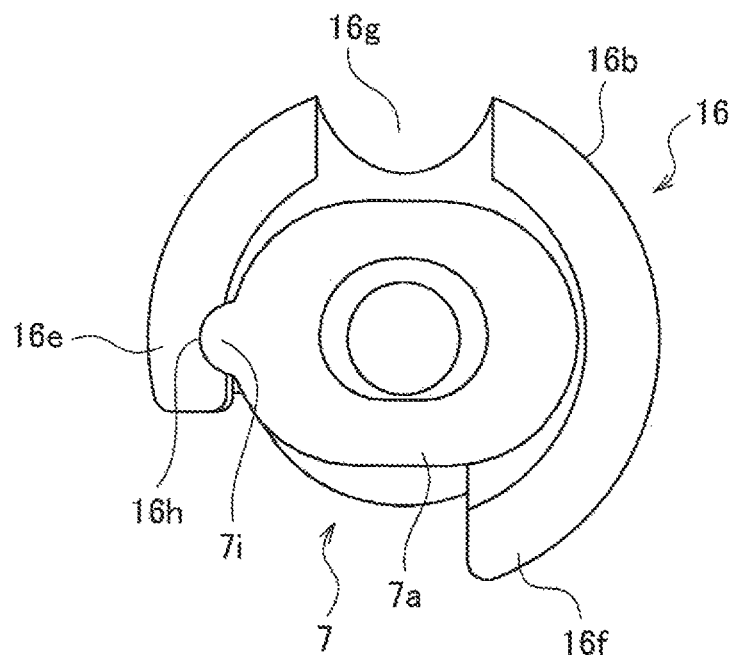
Figure 12B:
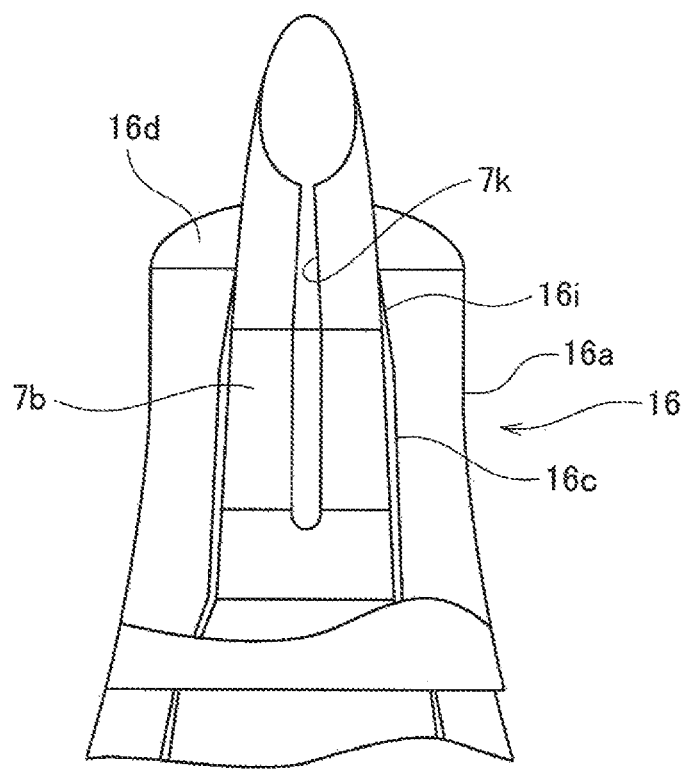

In such a case, an inner diameter of the through hole 16c of the sleep portion 16a may be set to be equal to or slightly larger than the outer circumferential diameter of the nozzle portion 7b over an entire axial length of the sleeve portion 16a, in order not to deform the shape of the nozzle portion 7b engaged with the through hole 16c. Further, as other preferable embodiment, as shown in FIG. 12A and FIG. 12B, a tapered portion 16i may be formed in a part of the through hole 16c of the sleeve portion 16a. The tapered portion 16i is formed such that the diameter of the through hole 16c is gradually decreased toward the tip of the sleeve portion 16a, on the tip side of the sleeve portion 16a. A minimum diameter of the through hole 16c in the tapered portion 16i is set to be smaller than an outer circumferential diameter of the nozzle portion 7b. Thereby, in a state in which the attachment member 16 is attached to the insertion tube 7, the tapered portion 16i comes into contact with the outer circumferential surface of the nozzle portion 7b and a portion where the cut portion 7k is formed. Therefore, on the tip side of the sleeve portion 16a, the outer circumference diameter of the sleeve portion 16a is reduced by a contact with the tapered portion 16i.

Meanwhile, the hook portion 16e of the engaging portion 16b is hooked on the first protrusion 7h. At this time, the recessed portion 16h is in a state of being engaged with the second protrusion 7i (see FIG. 12A). Further, the stopper portion 16f of the engaging portion 16b is in a state of approaching or contacting the third protrusion 7j of the injection tube 7. At this time, positioning of the attachment member 16 with respect to the injection tube 7 is performed as follows. Namely, in the direction around the axis of the injection tube 7, the position of the attachment member is determined when the recessed portion 16h is engaged with the second protrusion 7i of the injection tube 7, and when the hook portion 16e is hooked on the first protrusion 7h of the injection tube 7. Further, in the axial direction of the injection tube 7, the position of the attachment member 16 is determined when the stopper portion 16f abuts on the third protrusion 7j.

Figure 13A:
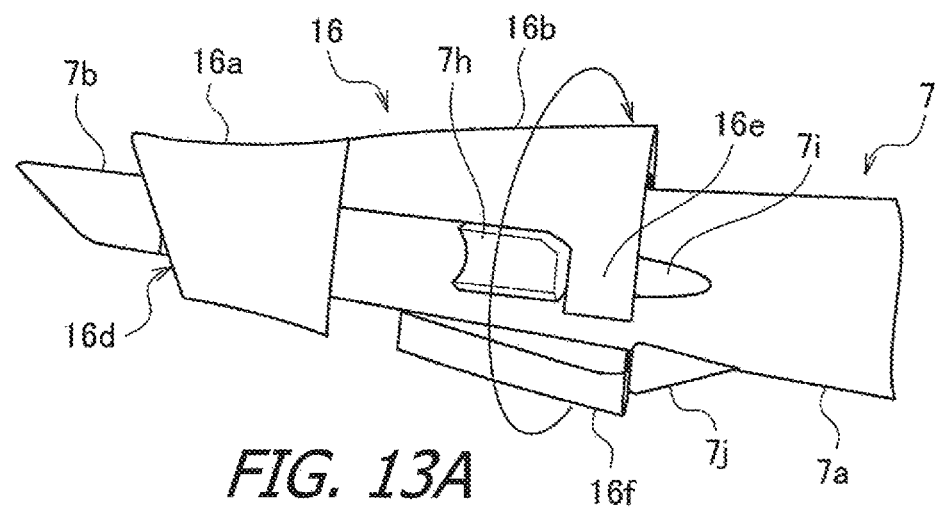
FIG. 13A to FIG. 13C are views for explaining a procedure of attaching and detaching the attachment member, respectively.
Figure 13B:
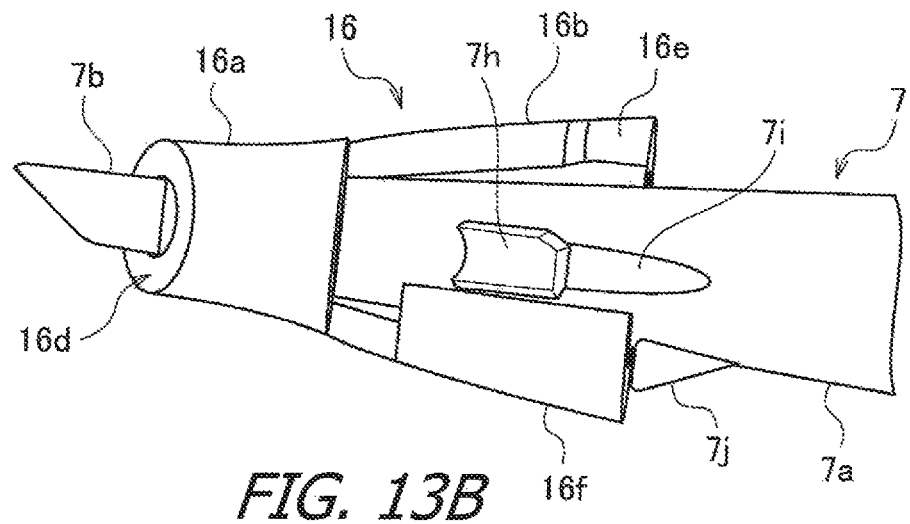
Figure 13C:
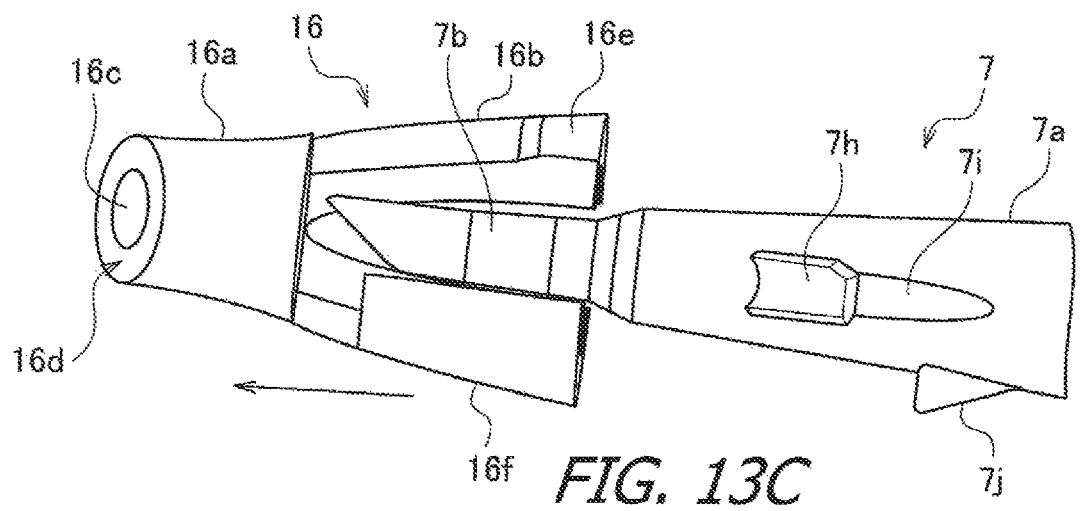

Here, when the attachment member 16 is detached from the insertion tube 7, the engagement state between the attachment member 16 and the insertion tube 7 is released by moving the attachment member 16 in the axial direction of the injection tube 7, after rotating the attachment member 16 in the direction around the axis of the injection tube 7. Specifically, first, the attachment member 16 is turned in a direction of the arrow as shown in FIG. 13A, thereby making the stopper portion 16f of the engaging portion 16b brought into contact with or close to the first protrusion 7h of the injection tube main body 7a as shown in FIG. 13B. Thereby, the hook portion 16e of the engaging portion 16b is disengaged from the first protrusion 7h of the injection tube 7, and the recessed portion 16h (see FIGS. 10A to 10C, 12A and 12B) inside of the hook portion 16e is disengaged from the second protrusion 7i. Next, as shown in FIG. 13C, the attachment member 16 is pulled out in the direction of the arrow along the axial direction of the injection tube 7. Thereby, the attachment member 16 can be detached from the injection tube 7.

Meanwhile, when the attachment member 16 is attached to the injection tube 7, the attachment member 16 is engaged with the injection tube 7 by a procedure reverse to the above, namely, the attachment member 16 is moved in the axial direction of the injection tube 7, and thereafter the attachment member 16 is rotated and moved in the direction around the axis of the injection tube 7. Specifically, the attachment member 16 is engaged with the injection tube 7 from the direction opposite to the arrow as shown in FIG. 13C, thereby making the stopper portion 16f of the engaging portion 16b brought into contact with or close to the third protrusion 7j of the injection tube 7 as shown in FIG. 13B. Next, by turning the attachment member 16 in the opposite direction to the direction of detachment, the hook portion 16e of the engaging portion 16b is hooked on the first protrusion 7h of the injection tube 7, and the recessed portion 16h is engaged with the second protrusion 7i. Thereby, the attachment member 16 can be attached to the injection tube 7. In this way, the attachment member 16 is attached to the injection tube 7, and in this state, the movement of the attachment member 16 with respect to the axial direction of the injection tube 7 is restricted due to the engagement (contact) between the first protrusion 7h and the hook portion 16e and due to the engagement (contact) between the third protrusion 7j and the stopper portion 16f. Therefore, the attachment member 16 cannot be moved in the axial direction of the injection tube 7. In other words, the position of the attachment member 16 is fixed in the axial direction of the injection tube 7. Further, the engagement state between the engaging portion 16b of the attachment member 16 and the engaging portion (7h, 7i, 7j) of the injection tube 7 is not released unless the attachment member 16 attached to the injection tube 7 is rotated in the direction around the axis of the injection tube 7, because it is impossible to move the attachment member 16 in the axial direction of the injection tube 7 as described above.

(Rotary Member)

Figure 14:
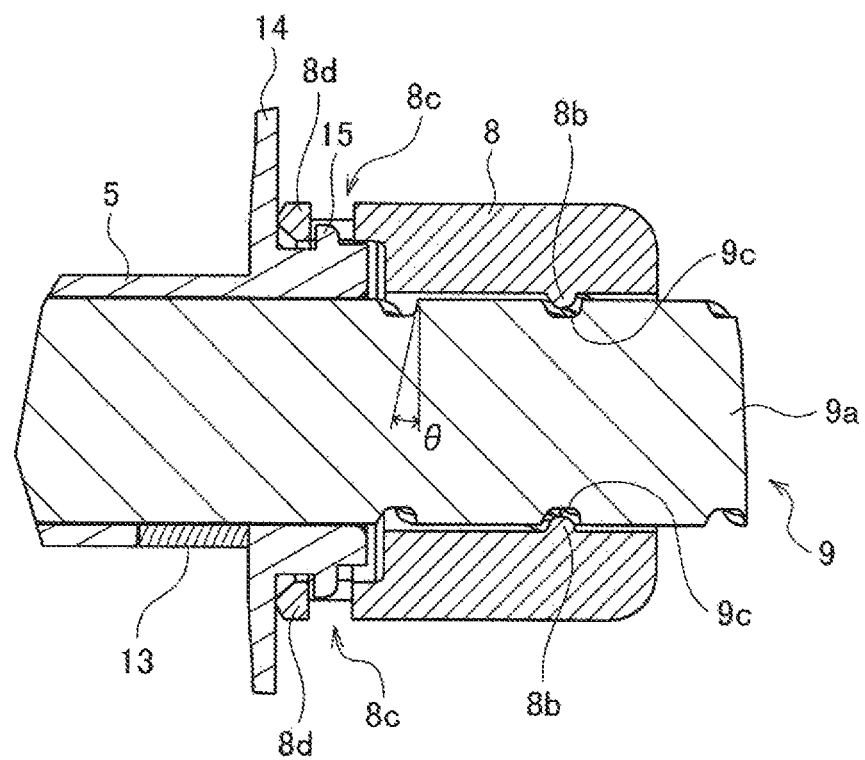
FIG. 14 is an enlarged view of a portion E5 in FIG. 2C.

As shown in FIG. 14, the rotary member 8 is attached to the rear end portion of the injector main body 5. In this attachment state, the rotary member 8 is disposed coaxially with the injector main body 5, and is rotatably supported in the direction around the axis of the injector main body 5. The rotary member 8 is formed in a cylindrical shape. The tip end and the rear end of the rotary member 8 are each opened in a circular shape. As shown in FIG. 1 and FIGS. 2A to 2C, a plurality of ridges 8a are formed on the outer circumferential surface of the rotary member 8. Each of the ridges 8a is formed to be parallel to the axial direction of the rotary member 8. The rotary member 8 is a portion rotated by a user when the intraocular lens injector 1 is used by a screw system. At this time, when the plurality of ridges 8a are formed on the outer circumferential surface of the rotary member 8, the finger of the user is caught on the ridges 8a, so that it becomes easy to rotate the rotary member 8.

First threaded portions 8b are formed on the inner circumferential surface of the rotary member 8. The first threaded portions 8b are formed at a predetermined pitch. Further, two window portions 8c are formed on the tip part of the rotary member 8. The two window portions 8c are formed at intervals of 180 degrees in the circumferential direction. These window portions 8c are portions for visually checking whether or not the injector main body 5 and the rotary member 8 are properly coupled. A pair of hooking claws 8d is formed on the inner circumferential portion of the tip of the rotary member 8. The pair of hooking claws 8d is hooked on the rotation supporting portion 15 of the injector main body 5 when the rotary member 8 is coupled to the rear end portion of the injector main body 5. Each of the hooking claws 8d is formed in the vicinity of the opening on the tip side of the rotary member 8 adjacent to each of the window portions 8c. The rotary member 8 is rotatably supported in the direction around the axis of the injector main body 5 in a state in which the pair of hook claws 8d are hooked on the rotation supporting portion 15. Further, the pair of hook claws 8d is fitted between the flange portion 14 of the injector main body 5 and the rotation supporting portion 15. Therefore, the rotary member 8 is freely rotatable around the axis of the injector main body 5 but does not move in the axial direction of the injector main body 5.

(Plunger)

Figure 15:
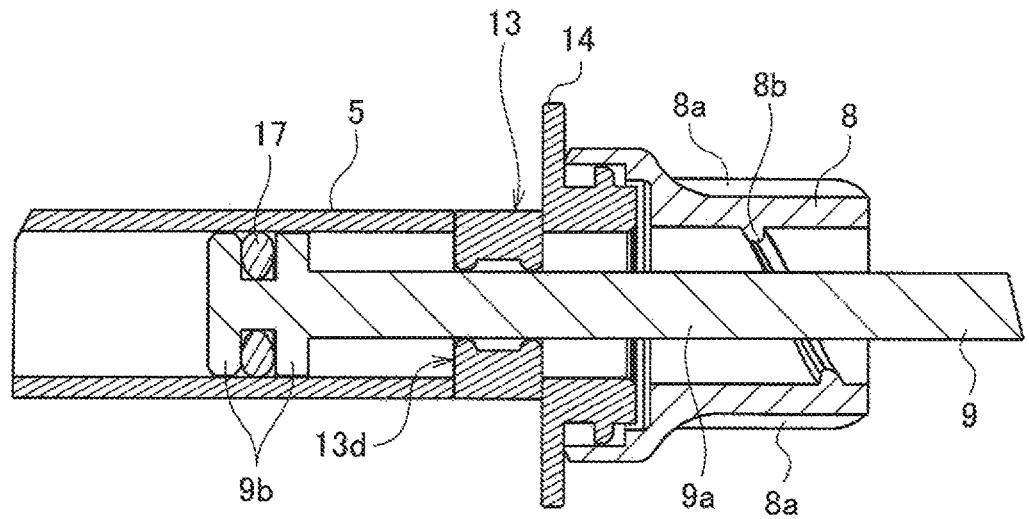
FIG. 15 is a cross-sectional view taken along the line E2-E2 in FIG. 2B.

The plunger 9 is disposed coaxially with the injector main body 5. The plunger 9 is provided movably in the axial direction of the injector main body 5. The plunger 9 has a bar shaped plunger shaft 9a. As shown in FIG. 15, the tip part of the plunger 9 serves as a seal material attachment portion 9b. FIG. 15 is a cross-sectional view taken along the line E2-E2 in FIG. 2B. The seal material attachment portion 9b is composed of two circular disk portions having an outer circumferential diameter slightly smaller than the inner diameter of the injector main body 5, and a seal member 17 is attached between the two disk portions. As the seal material 17, for example, an O ring can be used. When the plunger 9 is moved in the axial direction (frontward) of the injector main body 5, the seal member 17 is brought into contact with the inner circumferential surface of the injector main body 5, thereby generating an appropriate sliding resistance.

Figures 16A, 16B:
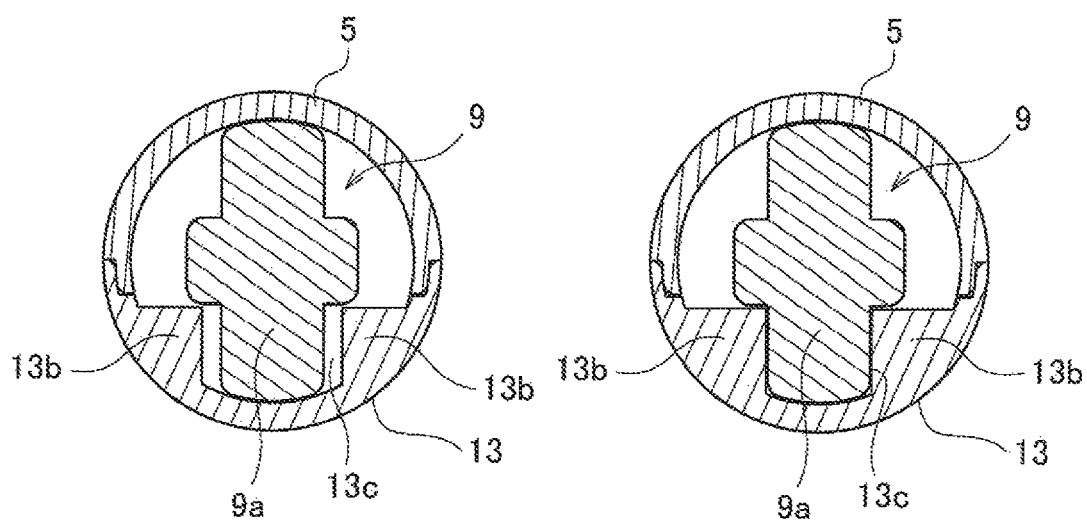
FIG. 16A is a cross-sectional view taken along line E3-E3 in FIG. 2B.
FIG. 16B is a cross-sectional view taken along the line E4-E4 in FIG. 2B.

The longitudinal sectional shape of the plunger shaft 9a is substantially cruciform as shown in FIG. 16A and FIG. 16B. FIG. 16A is a cross-sectional view taken along the line E3-E3 in FIG. 2B, and FIG. 16B is a cross-sectional view taken along the line E4-E4 in FIG. 2B. As shown in FIG. 1 and FIGS. 2A to 2C, second threaded portions 9c are formed on the upper surface and the lower surface of the plunger shaft 9a, respectively. The second threaded portions 9c are formed corresponding to the first threaded portions 8b of the rotary member 8. Therefore, the second threaded portions 9c are formed at the same pitch as the first threaded portions 8b. The second threaded portions 9c are held in a state of constantly meshing with the first threaded portions 8b of the rotary member 8. Therefore, when the rotary member 8 is rotated, the plunger 9 moves in the axial direction of the injector main body 5 in accordance with a rotation direction and a rotation amount of the rotary member 8. The plunger 9 is a portion to be pushed in by the user when using the intraocular lens injector 1 by the push system. Here, the second threaded portions 9c of the plunger 9 and the corresponding first threaded portions 8b of the rotary member 8 mesh with each other in a relationship of groove threads and screw threads, and in this meshing portion, the first threaded portions 8b and the second threaded portions 9c are inclined at a predetermined taper angle with respect to the Z axis (vertical direction in the figure) as shown in FIG. 14. When the taper angle of these screw portions 8b, 9c is adjusted (set) to an appropriate angle, it is possible to rotate the rotary member 8 with little sense of resistance when the plunger 9 is pushed in. Particularly, in a case of 5° or more and 15° or less of the taper angle θ at the rear of the second threaded portions 9c in contact with the first threaded portions 8b of the rotary member 8 when the plunger 9 is pushed in, the rotary member 8 idles without catching the threaded portions 8b, 9c, at the time of a forward movement of the plunger 9 by the pushing operation, which is preferable. Further, in order to efficiently apply a load to the rotary member 8, which is necessary for moving the plunger 9 forward by the pushing operation, it is desirable to set a groove width (dimension in the Y axis direction) between the threaded portions 9c of the plunger 9 to 1.0 mm or more and 4.0 mm or less. Also, regarding a screw pitch, it is desirable to adjust the screw pitch in accordance with a release load of an installed intraocular lens.

The tip side of the plunger 9, including the seal member attachment portion 9b, is disposed so as to be inserted into the injector main body 5, and the rear end side of the plunger 9 is disposed so as to protrude rearward from the rotary member 8. In an initial state before use, a protruding dimension Lp (see FIG. 2B) of the plunger 9 with a rear end position of the rotary member 8 as a reference, is set to be equal to or larger than a movement dimension of the rod 10 required to push out the intraocular lens 4 from the tip of the injection tube 7. Here, the initial state before use refers to a state before an operation is performed for pushing out the intraocular lens 4 using the rod 10 when using the intraocular lens injector 1. In the intraocular lens injector 1 of this embodiment, the rod 10 can be moved forward by either of the rotational operation of the rotary member 8 and the pushing operation of the plunger 9. Therefore, the initial state before use is the state in which neither the rotational operation of the rotation member 8 nor the pushing operation of the plunger 9 is performed.

In the initial state before use, the plunger 9 is largely drawn out so that the protruding dimension Lp of the plunger shaft 9a is substantially maximum or close to the maximum. In this state, the seal material attachment portion 9b of the plunger 9 is disposed in a state of being in proximity to or in contact with the rotation restricting portion 13 of the injector main body 5. At this time, the seal material attachment portion 9b of the plunger 9 is opposed to the anti-falloff portions 13d of the rotation restricting portion 13. Therefore, when attempting to move the plunger 9 rearward from the initial state before use, the seal material attachment portion 9b abuts on the anti-falloff portions 13d. Thereby, fall-off of the plunger 9 from the injector main body 5 is prevented.

Further, when the tip side of the plunger 9 is inserted into the injector main body 5 together with the rod 10, as shown in FIG. 5 FIGS. 5A and 5B, the rotation restricting portion 13 is set in an opened state. Thereby, the tip side of the plunger 9 with the seal member 17 can be inserted into the injector main body 5 without interference with the rotation restricting portion 13. Further, in this state, when the rotation restricting portion 13 is closed so as to be engaged with the plunger shaft 9a of the plunger 9, as shown in FIG. 16A and FIG. 16B, a part of the plunger shaft 9a (a portion where the second threaded portion 9c is formed) is engaged with the guide groove 13c of the sliding guide 13b. At this time, as shown in FIG. 16B, the two opposing surfaces of the guide groove 13c are disposed so as to support a part of the plunger shaft 9a from both sides. Thereby, the plunger 9 is supported movably in the axial direction of the injector main body 5. However, the rotation of the plunger 9 with respect to the axial direction of the injector main body 5 is restricted by the rotation restricting portion 13.

(Rod)

The rod 10 serves as releasing the intraocular lens 4 from the tip part (opening of the nozzle portion 7b) of the injection tube 7, by pushing out the intraocular lens 4 forward, the intraocular lens 4 being installed on the lens installing portion 11. The rod 10 is formed in an elongated rod shape. The rod 10 is coupled to the tip part of the plunger 9 and moves integrally with the plunger 9 in the axial direction of the hollow body.

<Method of Using the Intraocular Lens Injector>

Next, a method of using the intraocular lens injector 1 will be described.

First, the user injects a viscoelastic substance into the injection hole 7c of the injection tube 7. Thereby, the viscoelastic substance is supplied to the intraocular lens 4 installed on the lens installing portion 11 of the injector main body 5.

Next, the user moves the slider 6 forward. Thereby, a lens abutting portion (not shown) formed at the tip part of the slider 6 comes into contact with the intraocular lens 4, and pushes out the intraocular lens 4 as it is. Then, the intraocular lens 4 is deformed into a predetermined shape. When the intraocular lens 4 is deformed by the movement of the slider 6 in this manner, the intraocular lens 4 can be easily folded into a desired shape when the intraocular lens 4 is pushed out by the rod 10 by a subsequent operation.

Next, the user operates the intraocular lens injector 1 by the push system or the screw system to move the rod 10 forward together with the plunger 9, thereby releasing the intraocular lens 4 from the nozzle portion 7b of the injection tube 7. At this time, the rod 10 is brought into contact with the intraocular lens 4 while moving forward, and pushes out the intraocular lens 4 as it is. Then, the intraocular lens 4 moves inside of the injection tube 7 while being folded into a predetermined shape, and is released from the opening at the tip of the nozzle portion 7b. Accordingly, the intraocular lens 4 can be injected into the eye in a small folded state by releasing the intraocular lens 4 in a state in which the nozzle portion 7b of the injection tube 7 is inserted into the incisional wound of the eyeball. Further, after intraocular injection, the intraocular lens 4 can be restored to its original shape by a restoring force of the intraocular lens 4 itself.

<Effect of First Embodiment>

Next, an effect of the intraocular lens injector 1 according to a first embodiment of the present invention will be described.

The intraocular lens injector 1 of this embodiment can cope with two different operation methods, that is, a screw system and a push system. The screw system is a method of pushing out the intraocular lens 4 by the rotational operation of the rotary member 8, and the push system is a method of pushing out the intraocular lens 4 by a pushing operation of the plunger 9. Therefore, in using the intraocular lens injector 1, a user who prefers the screw system can push out the intraocular lens 4 by rotating the rotary member 8, and a user who prefers the push system can push out the intraocular lens 4 by pushing the plunger 9. Each operation method will be described below.

(Screw System)

When the intraocular lens injector 1 is used by the screw system, the user rotates the rotary member 8. Specifically, while rotating the injector body 5 with one hand, the rotary member 8 is rotated with the other hand. At this time, the first threaded portions 8b of the rotary member 8 and the second threaded portions 9c of the plunger 9 are always kept in mesh with each other, including the initial state before use. Therefore, when the rotary member 8 is rotated in a predetermined direction (clockwise direction as seen from the rear end side of the intraocular lens injector 1), the plunger 9 moves forward in accordance with the rotation of the rotary member 8, and the rod 10 also moves forward together with the movement of the plunger 9. Further, since the rotation of the plunger 9 in the direction around the axis of the injector main body 5 is restricted by the rotation restricting portion 13, the plunger 9 and the rod 10 move forward without rotating in the direction around the axis of the injector main body 5. Thereby, the intraocular lens 4 installed on the lens installing portion 11 of the injector main body 5, is pushed out from the tip of the nozzle portion 7b by the movement of the rod 10.

(Push System)

When the intraocular lens injector 1 is used by the push system, an operation of pushing the plunger 9 is performed by the user. Specifically, a thumb is pressed against the rear end portion of the plunger 9 while hooking an index finger and a middle finger on the flange portion 14 of the injector main body 5. Then, in this state, the plunger 9 is pushed forward. Then, a pushing force applied to the plunger 9 is converted to a force for rotating the rotary member 8 by the meshing between the first threaded portions 8b and the second threaded portions 9c. Therefore, when the plunger 9 is pushed forward, the plunger 9 moves forward together with the rod 10 and the rotary member 8 rotates in accordance with the movement of the plunger 9. Further, since the rotation of the plunger 9 in the direction around the axis of the injector main body 5 is restricted by the rotation restricting portion 13, the plunger 9 and the rod 10 move forward without rotating in the direction around the axis of the injector main body 5. Thereby, the intraocular lens 4 installed on the lens installing portion 11 of the injector main body 5, is pushed out from the tip of the nozzle portion 7*b* by the movement of the rod 10.

In this manner, the intraocular lens injector 1 of this embodiment can cope with either one of the operation methods such as the screw system and push system. Accordingly, the user of the intraocular lens injector 1, can select either one of the operation methods, according to his/her preference, or according to other reasons, circumstances etc. Thereby, with one intraocular lens injector 1, it is possible to flexibly cope with differences in procedures of an intraocular lens injection surgery. Further, it is possible to cater to both users of the user who prefers the screw system and the user who prefers the push system. Further, the first threaded portions 8*b* of the rotary member 8 and the second threaded portions 9*c* of the plunger 9, are always in mesh with each other, including the initial state before use. Therefore, in the case of operating by the screw system, the intraocular lens 4 can be pushed out only by rotating the rotary member 8. Further, in the case of operating by the push system, the first threaded portions 8*b* and the second threaded portions 9*c* are held in mesh with each other from the start to the end of the operation. Therefore, vibration or the like is unlikely to occur during the pushing operation of the plunger 9.

(Nozzle Insertion Amount Limiting Function of the Attachment Member)

According to the intraocular lens injector 1 of this embodiment, it is possible to utilize the nozzle insertion amount limiting function provided by the attachment member 16 or to avoid its use. Specifically, the attachment member 16 is configured to be movable with respect to the injection tube 7, thereby making it possible to attach and detach the attachment member 16 to/from the injection tube 7. Therefore, in the state in which the attachment member 16 is attached to the injection tube 7, the nozzle insertion amount limiting function can be used, and in the state in which the attachment member 16 is detached from the injection tube 7, use of the nozzle insertion amount limiting function can be avoided. Explanation will be given hereinafter for a case of using the nozzle insertion amount limiting function and a case of not using the nozzle insertion amount limiting function separately.

(Case of Using the Nozzle Insertion Amount Limiting Function)

Figure 17:
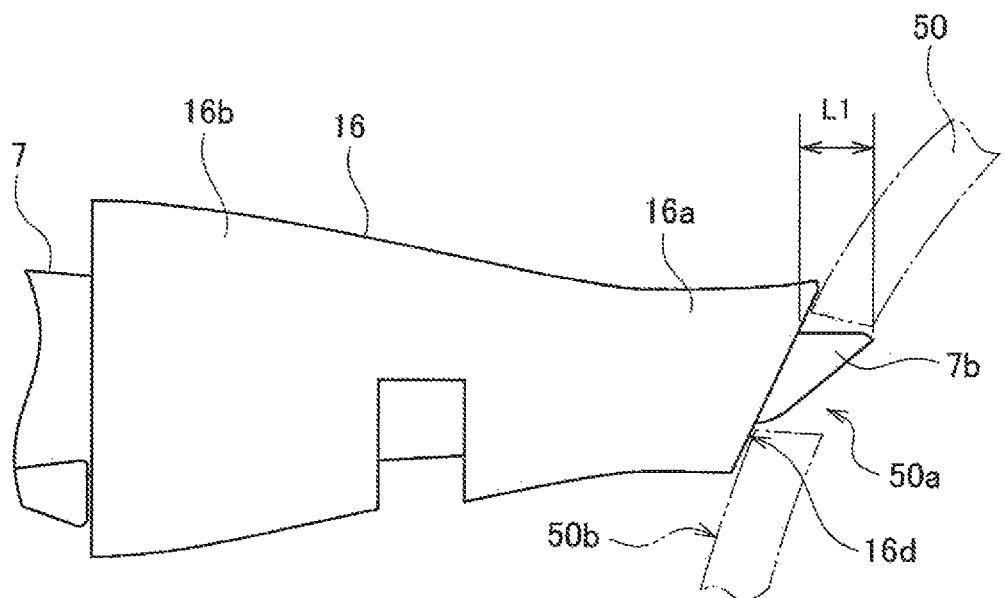
FIG. 17 is a view for explaining a function of the attachment member.

When using the nozzle insertion amount limiting function provided by the attachment member 16, the attachment member 16 is set in a state of being attached to the injection tube 7. Thereby, the nozzle portion 7*b* of the injection tube 7 is partially covered with the sleeve part 16*a* of the attachment member 16. The nozzle insertion amount limiting function is exhibited by contact of the tip surface 16*d* of the sleeve part 16*a* with the outer surface 50*b* of the cornea 50, when an incisional wound 50*a* is formed in the periphery of the cornea 50 of the eyeball, and the nozzle portion 7*b* of the injection tube 7 is inserted into the incisional wound 50*a* in a cataract surgery as shown in FIG. 17. At this time, the tip surface 16*d* of the sleeve part 16*a* functions as a stopper for limiting further insertion of the nozzle portion 7*b*, by contact of the tip surface 16*d* of the sleeve part 16*a* with the outer surface 50*b* of the cornea 50, and by this stopper function, the insertion amount of the nozzle portion 7*b* is limited.

Here, when the Wound-assisted method is applied, it is desirable to set a relative position of the injection tube 7 and the attachment member 16, so that the protruding amount (Maximum value) L1 of the nozzle portion 7*b* with respect to the tip surface 16*d* of the sleeve part 16*a* is 1.0 mm or more and 1.2 mm or less. Thereby, it is possible to limit the insertion amount of the nozzle portion 7*b* with respect to the incisional wound 50*a* of the cornea 50 to be equivalent to the protrusion amount L1. Accordingly, the intraocular lens 4 can be released from the tip of the nozzle portion 7*b* in a state of shallowly inserting the nozzle portion 7*b* into the incisional wound 50*a* of the cornea 50. Further, in order to use the nozzle insertion amount limiting function, the movement of the attachment member 16 with respect to the axial direction of the insertion tube 7 is restricted by the engagement between the first protrusion 7*h* and the hook portion 16*e* and the engagement between the third protrusion 7*j* and the stopper portion 16*f* in a state in which the attachment member 16 is attached to the injection tube 7. Therefore, after the intraocular lens 4 is released from the tip of the nozzle portion 7*b*, the tip surface 16*d* of the attachment member 16 can be separated from the outer surface 50*b* of the cornea 50 simultaneously with pulling out the nozzle portion 7*b* from the incisional wound 50*a* of the cornea 50. Further, when using the nozzle insertion amount limiting function, as described above, the injection tube 7 and the attachment member 16 are used in a combined state. Therefore, the engaging portion 16*b* of the attachment member 16 and the engaging portion (7*h*, 7*i*, 7*j*) of the injection tube 7 are always maintained in an engagement state, and the engagement state is not canceled.

(Case of Not Using the Nozzle Insertion Amount Limiting Function)

Meanwhile, when the nozzle insertion amount limiting function provided by the attachment member 16 is not used, the attachment member 16 is detached from the injection tube 7. Thereby, the nozzle portion 7*b* of the injection tube 7 is in a state in which its entire body is exposed to the outside without being covered by the sleeve portion 16*a* of the attachment member 16. Therefore, when the nozzle portion 7*b* of the injection tube 7 is inserted into the incisional wound 50*a* of the cornea 50, the nozzle portion 7*b* can be inserted more deeply than in the case of using the nozzle insertion amount limiting function described above. Accordingly, the intraocular lens 4 can be released from the tip of the nozzle portion 7*b* in a state in which the nozzle portion 7*b* is deeply inserted into the incisional wound 50*a* of the cornea 50.

In this manner, in the intraocular lens injector 1 of this embodiment, the nozzle insertion amount limiting function can be used by attaching the attachment member 16 to the insertion tube 7, and in addition, use of the nozzle insertion amount limiting function can be avoided by detaching the attachment member 16 from the injection tube 7. Accordingly, the user of the intraocular lens injector 1, can use the nozzle insertion amount limiting function or to avoid using it, according to his/her preference, or according to other reasons, circumstances etc. Thereby, even if there are user who prefers the procedure for inserting the nozzle portion 7*b* deeply into the incisional wound 50*a* of the eye ball and user who prefers the procedure to shallowly insert the nozzle portion 7*b*, it is possible to flexibly deal with the preference of each user's technique.

Figure 18:
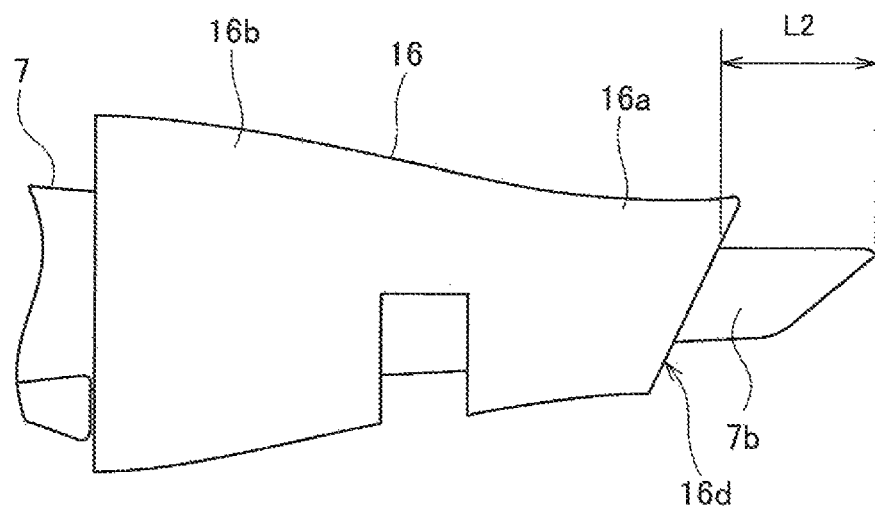
FIG. 18 is a view showing an example of changing a protrusion amount of the nozzle member.

Further, if a plurality of attachment members 16 having different sizes (particularly, lengths) of the sleeve portions 16a are prepared, it is possible to change (increase or decrease) the protrusion amount of the nozzle portion 7b with respect to the tip surface 16d of the sleeve portion 16a, depending on the size of attached member 16 attached to injection tube 7 when using the nozzle insertion amount limiting function. For example, when it is desired to change the protrusion amount to a protrusion amount (for example, 5.0 mm or more and 6.5 mm or less) larger than the protrusion amount L1 of the nozzle portion 7b shown in FIG. 17, as shown in FIG. 18, the protrusion amount (maximum value) L2 of the nozzle portion 7b can be secured to be larger than the protrusion amount L1 by using the attachment member 16 having a size compatible with the above protruding amount, for attachment to the injection tube 7. Thereby, the insertion amount can be changed when inserting the nozzle portion 7b into the incisional wound 50a of the cornea 50.

The intraocular lens injector 1 of this embodiment exhibits the effect of (hereinafter referred to as a "first effect") enabling selection of the operation method of the intraocular lens injector 1 from the screw system and the push system, and the effect of (hereinafter referred to as a "second effect") enabling selection as to whether or not to use the nozzle insertion amount limiting function. However, the first effect and the second effect are obtained by different configurations. Namely, the first effect is obtained by a configuration (hereinafter referred to as "first configuration") including the injector main body 5, the rotary member 8, the plunger 9, and the rod 10 described above, and the second effect is obtained by a configuration (hereinafter referred to as a "second configuration") including the injection tube 7 and the attachment member 16 described above. Therefore, the first effect can be obtained even without the second configuration and the second effect can be obtained even without the first configuration.

Further, this embodiment employs a configuration in which the outer circumferential diameter of the nozzle portion 7b can be reduced by forming the tapered portion 16i in the through hole 16c of the attachment member 16 and bringing the tapered portion 16i into contact with the outer circumferential surface of the nozzle portion 7b. Thereby, even if the size of the incisional wound formed on the eyeball is reduced, the tip part of the nozzle portion 7b can be easily inserted into the incisional wound. Further, when the intraocular lens 4 is passed through the nozzle portion 7b in a folded state in a predetermined shape, the nozzle portion 7b is pressed by the intraocular lens 4 from the inside and is deformed. At this time, if the cutout portion 7k is formed in the nozzle portion 7b, even if the nozzle portion 7b is pressed by the intraocular lens 4 and is deformed, damage such as cracks and the like are less likely to occur in the nozzle portion 7b. Further, an amount of deformation of the nozzle portion 7b is suppressed to minimum necessary for releasing the intraocular lens 4. Therefore, the intraocular lens 4 can be injected from a smaller incisional wound.

Further, this embodiment employs a configuration in which a viewing window 16g is formed on the attachment member 16. Therefore, even when the intraocular lens injector 1 is used with the attached member 16 attached to the injection tube 7, the state of the intraocular lens 4 moving inside of the insertion tube 7 can be visually recognized from the outside through the viewing window 16g. Accordingly, the user of the intraocular lens injector 1 can operate the intraocular lens injector 1 while visually checking the state of the intraocular lens 4 pushed out by the rod 10, even when the attachment member 16 is attached.

<Second Embodiment>

Next, a second embodiment of the present invention will be described.

Figure 19:
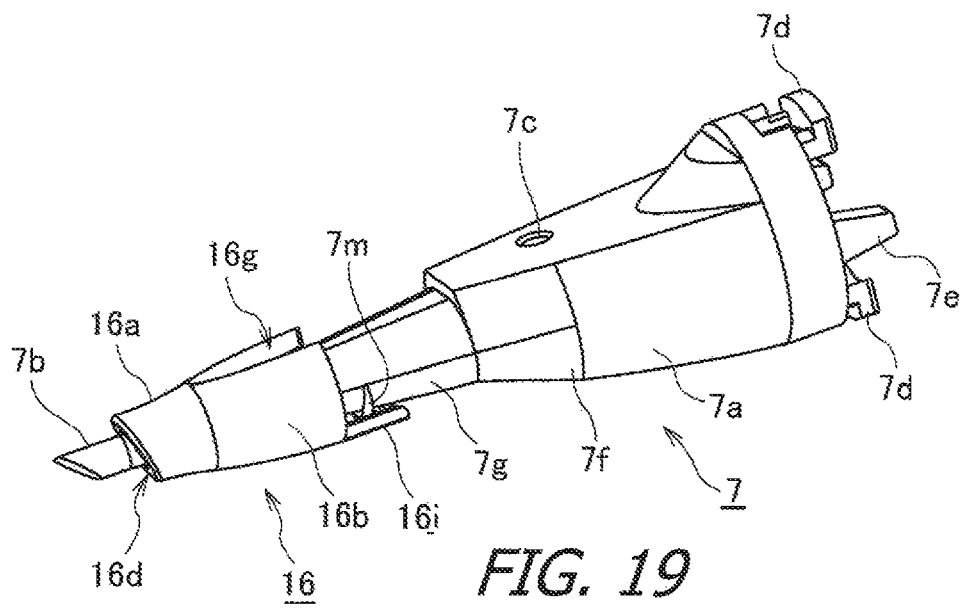
FIG. 19 is a perspective view showing a state in which the attachment member is attached to the injection tube in the intraocular lens injector according to a second embodiment of the present invention.

FIG. 19 is a perspective view showing a state in which the attachment member is attached to the injection tube in the intraocular lens injector according to a second embodiment of the present invention. Hereinafter, the configuration of the injection tube and the attachment member according to the second embodiment of the present invention will be described in detail.

(Injection Tube)

Figure 20:
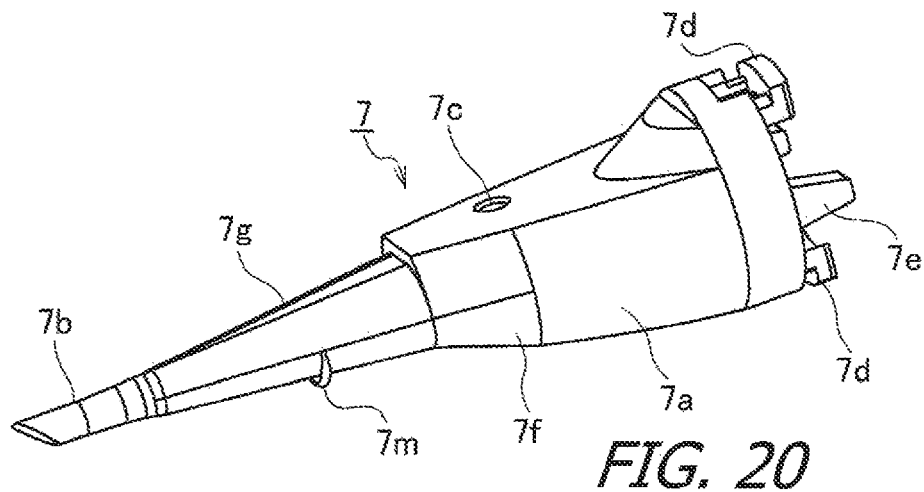
FIG. 20 is a perspective view showing a configuration of the injector tube according to the second embodiment of the present invention.
Figure 21:
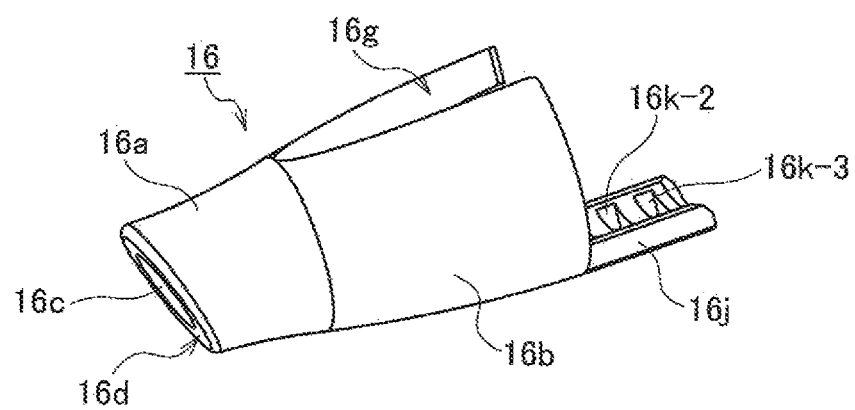
FIG. 21 is a perspective view showing a configuration of the attachment member according to the second embodiment of the present invention.

FIG. 20 is a perspective view showing the configuration of the injector tube according to the second embodiment of the present invention.

The injection tube 7 differs from that of the first embodiment only in the configuration of the engaged portion. Namely, the first embodiment employs a configuration in which the engaged portion is configured by three protrusions 7h, 7i, 7j, but the second embodiment employs a configuration in which the engaged portion is configured by one locking claw 7m. The locking claw 7m is formed in a substantially U-shape from both side surfaces to the lower surface of the second portion 7g of the injection tube main body 7a, when viewed from the front. Further, the locking claw 7m is formed to protrude downward from the lower surface of the second portion 7g.

(Attachment Member)

Figure 22A:
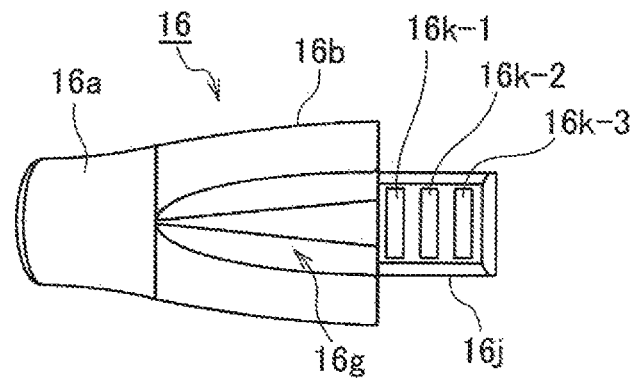
Figure 22B:
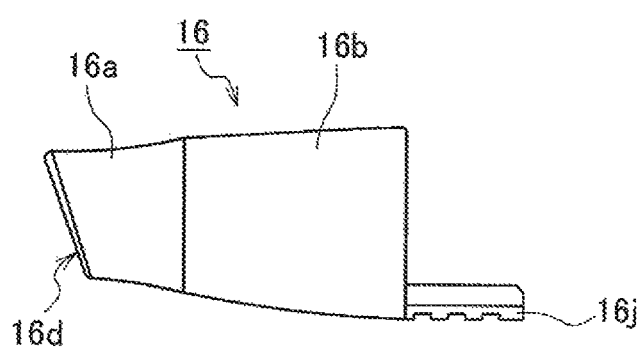
Figure 22D:
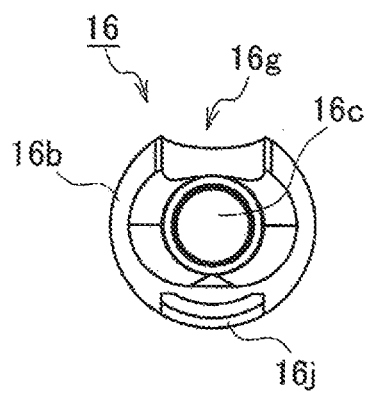
Figure 22C:
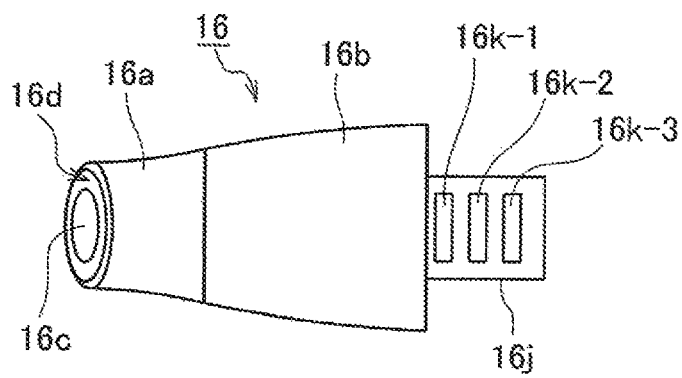

FIGS. 21A to 22D are perspective views showing the configuration of the attachment member according to the second embodiment of the present invention. Further, FIG. 22 shows the configuration of the attachment member according to the second embodiment of the present invention, wherein FIG. 22A is a plan view, FIG. 22B is a side view, FIG. 22C is a bottom view, and FIG. 22D is a rear view.

The attachment member 16 includes a sleeve portion 16a and an engaging portion 16b similarly to the first embodiment, but the configuration of the engaging portion 16b is different. Namely, in the engaging portion 16b, a tongue piece 16j is integrally formed in addition to the viewing window 16g, but the hook portion 16e and the stopper portion 16f are not formed. The tongue piece 16j is formed so as to extend from the lower portion of the engaging portion 16b in the axial direction of the attachment member 16. The tongue piece 16j is formed in a ladder shape having three engagement holes 16k. In the following description, the three engagement holes 16k are distinguished by identification codes such as 16k-1, 16k-2, and 16k-3. The three engagement holes 16k-1, 16k-2, and 16k-3 are formed side by side so as to be adjacent to each other with a predetermined interval in the axial direction of the attachment member 16. Further, the three engagement holes 16k-1, 16k-2, and 16k-3 are sequentially disposed from the front toward the rear in the axial direction of the attachment member 16. The attachment member 16 has a configuration in which the locking claw 7m of the injection tube 7 is engaged with any one of the three engagement holes 16k-1, 16k-2, and 16k-3, thereby being engaged with the injection tube 7.

Figure 23A:
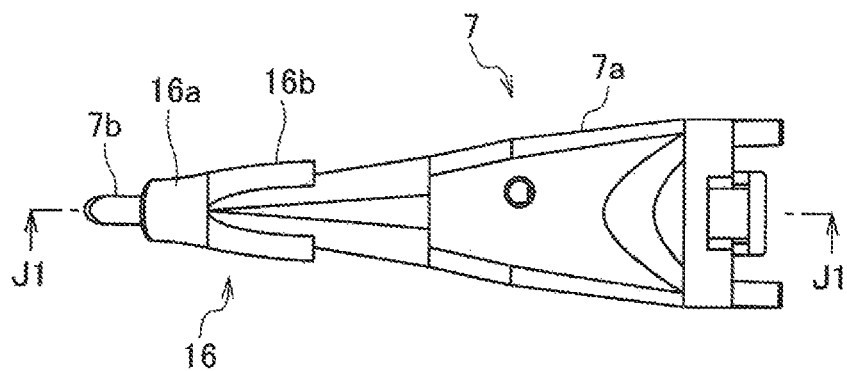
Figure 23B:
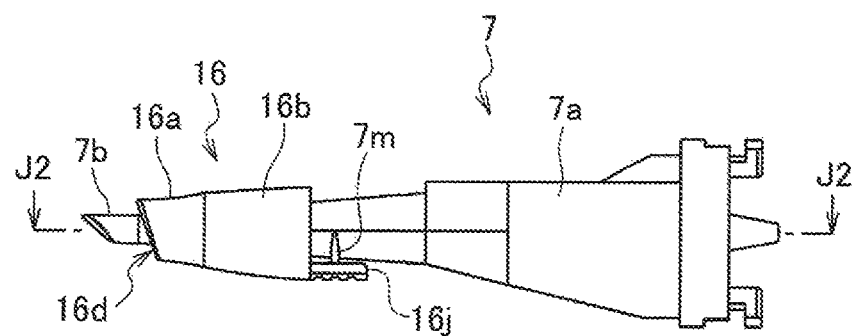
Figure 23C:
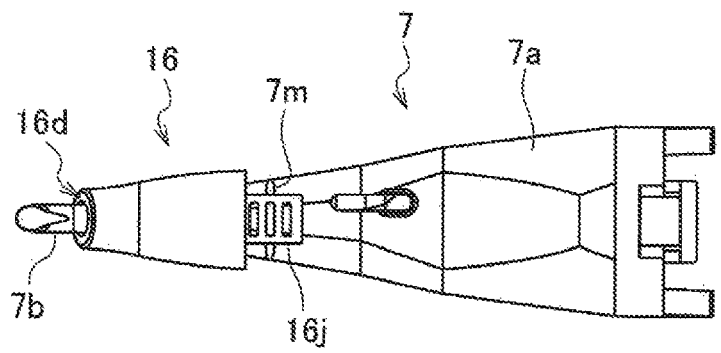
Figure 24A:
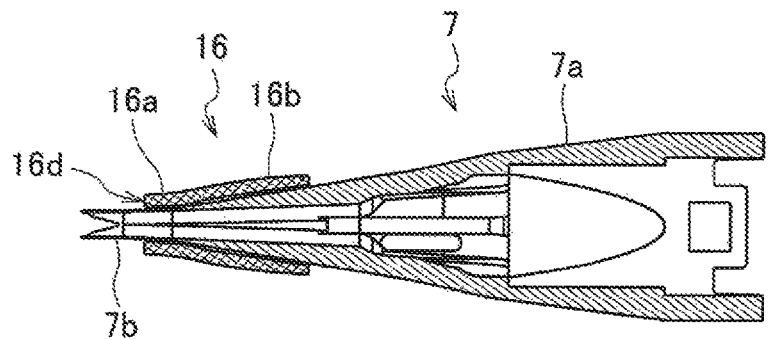
FIG. 24A is a cross-sectional view taken along the line J2-J2 in FIG. 23B.
Figure 24B:
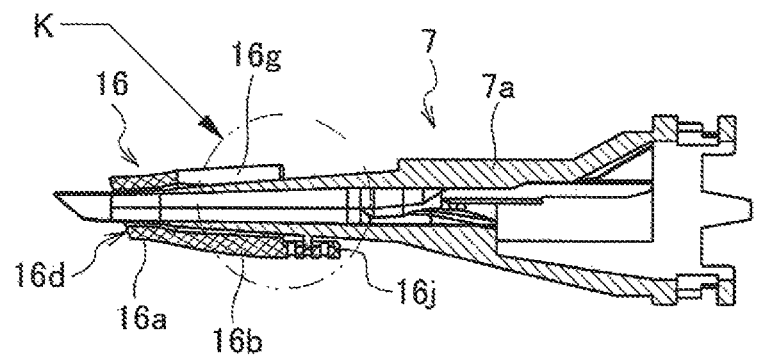
FIG. 24B is a cross-sectional view taken along the line J1-J1 in FIG. 23A.
Figure 24C:
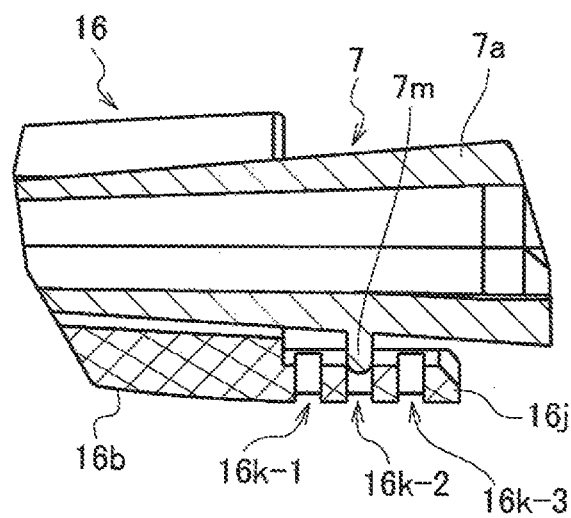
FIG. 24C is an enlarged view of portion K in FIG. 24B.

FIGS. 23A to 23C show a state in which the attachment member is attached to the injection tube, wherein FIG. 23A is a plan view, FIG. 23B is a side view, and FIG. 23C is a bottom view. Further, FIG. 24A is a cross-sectional view taken along the line J2-J2 in FIG. 23B, FIG. 24B is a cross-sectional view taken along the line J1-J1 in FIG. 23A, and FIG. 24C is an enlarged view of portion K in FIG. 24B.

In the state in which the attachment member 16 is attached to the injection tube 7 as shown in the figure, the nozzle portion 7b is fitted into the through hole 16c of the sleeve portion 16a. Further, the locking claw 7m formed on the injection tube 7 is engaged with the central engaging hole 16k-2 among the three engagement holes 16k-1, 16k-2, and 16k-3 formed on the tongue piece 16j of the attachment member 16. At this time, the tip surface 16d of the sleeve portion 16a is disposed to protrude outward from the outer circumferential surface of the nozzle portion 7b, and is disposed in a state inclined in the same direction as the cutout of the nozzle portion 7b with respect to the axial direction of the injection tube 7.

Figure 25A:
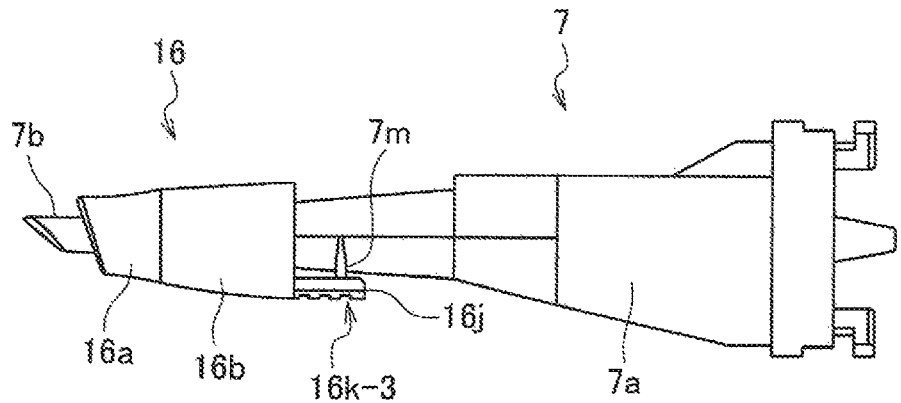
FIG. 25A is a side view showing a state in which a locking claw is engaged with a rear engagement hole.
Figure 25B:
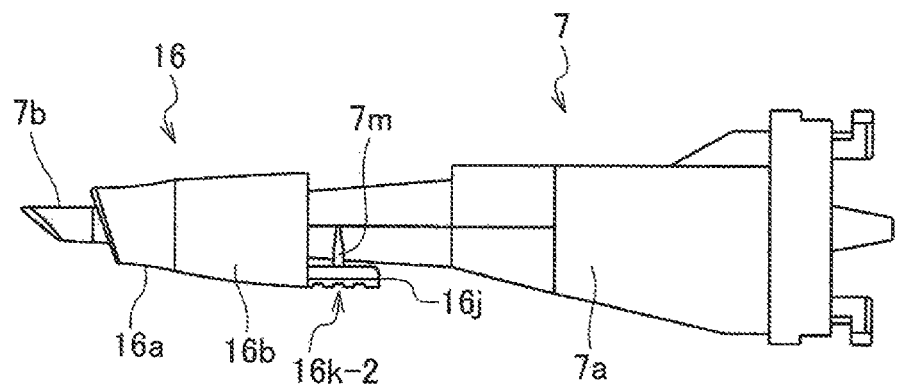
FIG. 25B is a side view showing a state in which the locking claw is engaged with a central engagement hole.
Figure 25C:
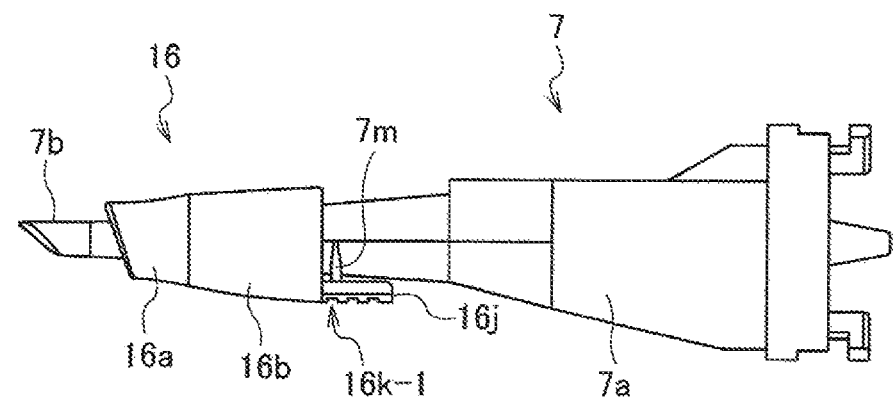
FIG. 25C is a side view showing a state in which the locking claw is engaged with a front engagement hole.

When using the nozzle insertion amount limiting function, the locking claw 7m is engaged with any one of the three engagement holes 16k-1, 16k-2, and 16k-3. In this case, the protrusion amount of the nozzle portion 7b with respect to the tip surface 16d of the sleeve portion 16a is changed depending on which engagement holes 16k is used for engagement with the locking claw 7m. FIG. 25A is a side view showing a state in which the locking claw 7m is engaged with the rear engagement hole 16k-3. In this state, the attachment member 16 is disposed relatively closer to the front in the axial direction of the injection tube 7. Therefore, the protrusion amount of the nozzle portion 7b becomes relatively small. In contrast, FIG. 25B is a side view showing a state in which the locking claw 7m is engaged with the central engagement hole 16k-2. In this state, the protrusion amount of the nozzle portion 7b becomes larger in the state of FIG. 25A. FIG. 25C is a side view showing a state in which the locking claw 7m is engaged with the front engaging hole 16k-1. In this state, the attachment member 16 is disposed relatively closer to the rear side in the axial direction of the injection tube 7. Therefore, the protrusion amount of the nozzle portion 7b becomes larger in the state of FIG. 25B.

As described above, in the second embodiment of the present invention, the protrusion amount of the nozzle portion 7b can be changed (adjusted) to three levels of large, medium, and small, by appropriately moving the attachment member 16 in the axial direction of the injection tube 7 so that the locking claw 7m is engaged with one of the engagement holes 16k of the tongue piece 16j. Further, if more engagement holes 16k are formed on the tongue piece 16j of the attachment member 16, the protrusion amount of the nozzle portion 7b can be changed in more stages. Further, if the attachment member 16 is pressed in the axial direction of the injection tube 7 in a state in which the locking claw 7m of the injection tube 7 is engaged with the central engagement hole 16k-2, the tongue piece 16j of the attachment member 16 is elastically deformed (bending deformation) upon receiving a pressing force, and as a result, the locking claw 7m is engaged with the adjacent engagement hole 16k-1 or 16k-3. Therefore, the protrusion amount of the nozzle portion 7b can be changed while the attachment member 16 is attached to the injection tube 7. Thereby, the protrusion amount of the nozzle portion 7b can be changed without attaching or detaching the attachment member 16 to or from the injection tube 7. Therefore, it is possible to save labor for detaching the attachment member 16 from the injection tube 7 and labor for placing the attachment member 16 on a tray or the like. Further, there is no risk of the user inadvertently dropping or losing the attachment member 16 detached from the injection tube 7.

Further, when the nozzle insertion amount limiting function is not used, for example, the entire body of the nozzle portion 7b can be exposed by releasing the engagement state between the locking claw 7m and the tongue piece 16j and pulling out the attachment member 16 from the injection tube 7. Alternatively, it is also acceptable that the entire body of the nozzle portion 7b is exposed when the attachment member 16 is moved backward by a predetermined amount while the attachment member 16 is attached to the injection tube 7, and in this state, the attachment member 16 is engaged with the injection tube 7 by the engagement between the locking claw 7m and the engagement hole 16k. When this configuration is employed, it is possible to switch whether or not to use the nozzle insertion amount limiting function without detaching the attachment member 16 from the injection tube 7. Therefore, the attachment member 16 is not required to be detachable from the injection tube 7.

<Third Embodiment>

Figure 27A:
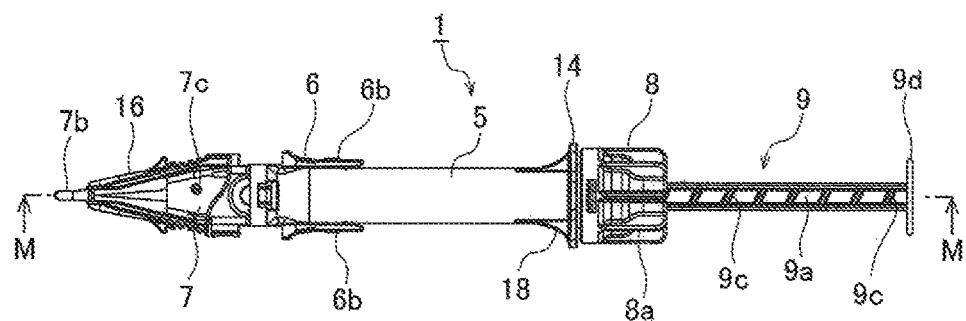
Figure 27B:
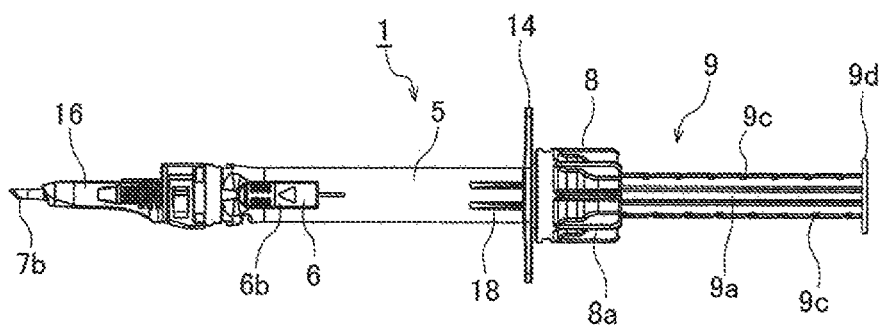
FIG. 27B is a side view.
Figure 27C:
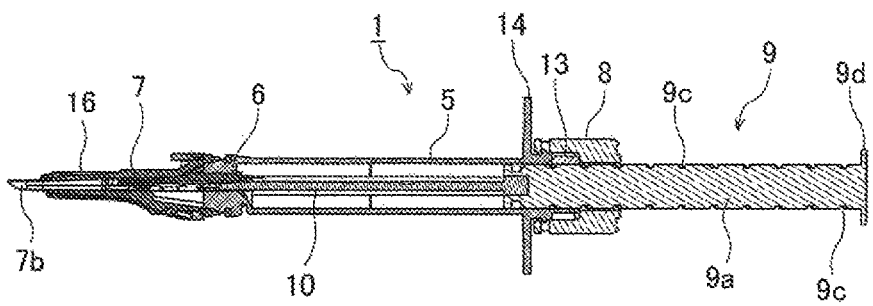
FIG. 27C is a cross-sectional view taken along the line M-M in in FIG. 27A.

FIG. 26 is a perspective view showing a configuration of the intraocular lens injector according to a third embodiment of the present invention. Further, FIG. 27A is a plan view showing the configuration of the intraocular lens injector according to the third embodiment of the present invention, wherein FIG. 27B is a side view, and FIG. 27C is a cross-sectional view taken along the line M-M in in FIG. 27A.

In the intraocular lens injector 1 according to the third embodiment of the present invention, a position and a configuration of the rotation restricting portion 13, a configuration of part of the plunger 9, a configuration of the injection tube 7, and a configuration of the attachment member 16 are different.

(Position and Configuration of the Rotation Restricting Portion)

Figure 28A:
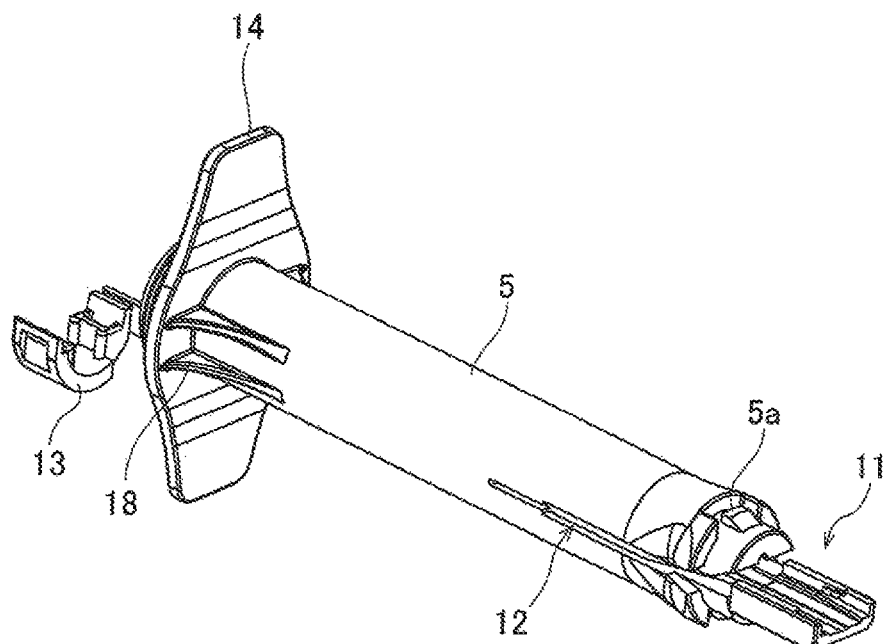
Figure 28B:
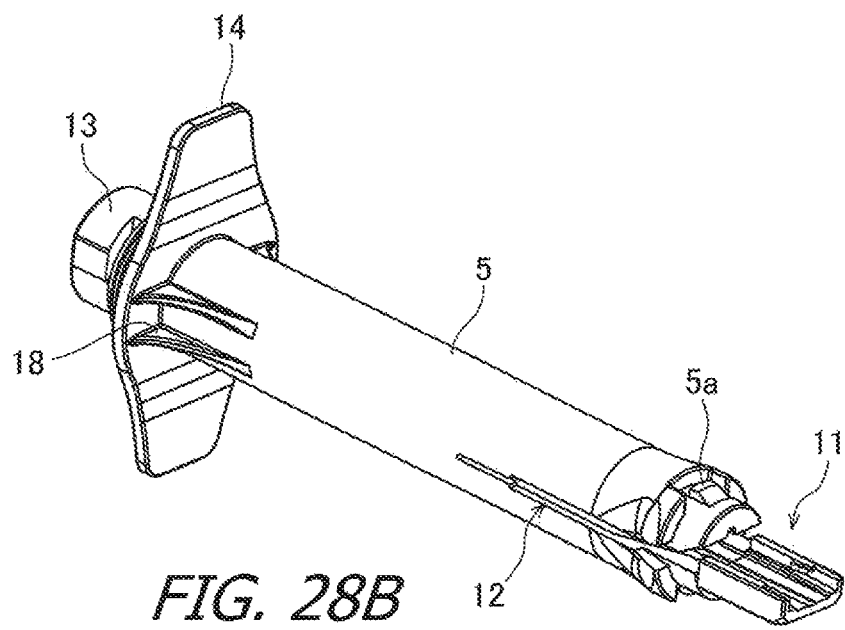

FIGS. 28A and 28B are perspective views showing a configuration of the injector main body according to the third embodiment of the present invention, FIG. 28A shows a state in which the rotation restricting portion provided in the injector main body is opened, and FIG. 28B shows a state in which the rotation restricting portion is closed.

The rotation restricting portion 13 is formed at the rear end portion of the injector main body 5 located slightly rearward of the flange portion 14 in the axial direction of the injector main body 5. When the rotary member 8 is attached to the rear end portion of the injector main body 5, the rotation restricting portion 13 is disposed inside of the rotary member 8 (see FIG. 27C). Therefore, the entire body of the rotation restricting portion 13 is shielded by the rotary member 8. The function, the configuration, and the like of the rotation restricting portion 13 are basically the same as those of the first embodiment.

As described above, by employing a configuration in which the rotation restricting portion 13 is formed at the rear end portion of the injector main body 5 and the rotation restricting portion 13 is shielded by the rotary member 8 attached thereto, it is possible to shorten a length of the injector main body 5 and reduce a size of the intraocular lens injector 1, compared to the first embodiment. Further, after assembling the intraocular lens injector 1, the rotation restricting portion 13 is hidden inside of the rotary member 8, and therefore the rotation restricting portion 13 cannot be opened. Therefore, it is possible to reduce the risk of decomposing the intraocular lens injector 1 by a surgeon or the like. Further, it is not necessary to form the rotation restricting portion 13 in front of the flange portion 14, and therefore it is possible to reinforce the flange portion 14 by forming reinforcing ribs 18 on the outer circumferential surface of the injector main body 5. Thereby, even when a strong force is applied to the flange portion 14 by the operation by the push system, deformation of the flange portion 14 can be suppressed.

Note that the third embodiment employs a configuration in which the entire body of the rotation restricting portion 13 is shielded by the rotary member 8. However, the present invention is not limited thereto, and it is possible to reduce the risk of decomposing the intraocular lens injector 1 by a surgeon or the like, as long as at least a part of the rotation restricting portion 13 is shielded by the rotary member 8. Further, the position of the rotation restricting portion 13 employed in the third embodiment can also be employed in the first embodiment and the second embodiment.

Figures 39A, 39B:
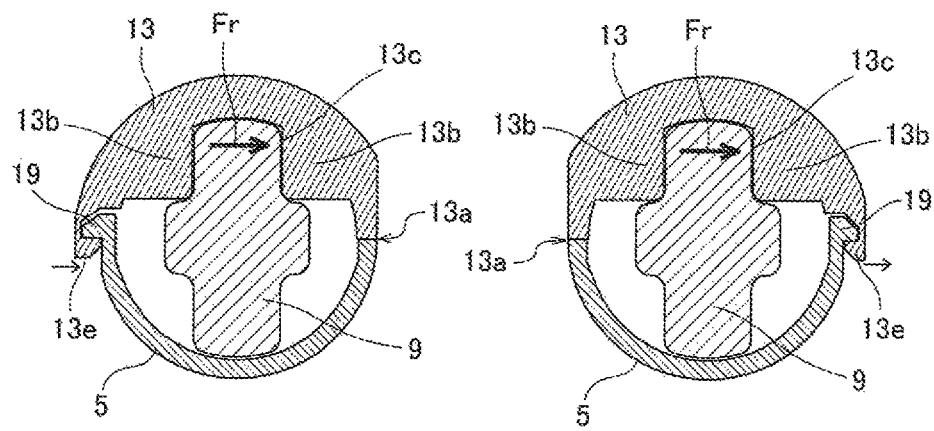
FIGS. 39A to 39D are section views showing an arrangement relationship between a plunger and a rotation restricting portion according to the third embodiment of the present invention.

Further, the third embodiment employs a hook mechanism, in order to hold the rotation restricting portion 13 in a closed state. For example as shown in FIG. 39A, the hook mechanism includes a first hook claw 13e formed in the rotation restricting portion 13 and a second hook claw 19 formed on the outer circumferential surface of the injector main body 5. FIGS. 39A to 39D each shows a case in which the rotation restricting portion 13 is viewed from behind the injector main body 5.

The first hook claw 13e is formed on the opposite side of the pivotally supporting portion 13a in the rotation restricting portion 13. The pivotally supporting portion 13a connects the rotation restricting portion 13 and the injector main body 5 and supports the rotation restricting portion 13 so as to be rotatable (openable and closable). The second hook claw 19 is formed on the opposite side of the pivotally supporting portion 13a in the left-right direction.

In the hook mechanism having the above configuration, when the rotation restricting portion 13 is closed from the opened state, the first hook claw 13e of the rotation restricting portion 13 is caught by the second hook claw 19 of the injector main body 5 and locked. At this time, in a radial direction of the injector main body 5, the first hook claw 13e is disposed relatively outside, and the second hook claw 19 is disposed relatively inside. Further, the plunger 9 is fitted into a guide groove 13c formed between the pair of sliding guides 13b of the rotation restricting portion 13. Therefore, when the rotary member 8 is rotated so as to use the intraocular lens injector 1 by the screw system, the rotation of the plunger 9 in the direction around the axis of the injector main body 5 is restricted by the rotation restricting portion 13.

Further, since the first threaded portions 8b of the rotary member 8 and the second threaded portions 9c of the plunger 9 are meshed with each other. Therefore, when the rotary member 8 is rotated so as to move the plunger 9 forward, a rotational force Fr is applied to the plunger 9 by the rotation of the rotary member 8. When the rotational force Fr is applied to the plunger 9, the rotation restricting portion 13 is pushed by the plunger 9. As a result, the first hook claw 13e of the rotation restricting portion 13 is pressed against the second hook claw 19. Therefore, it is possible to hold the first hook claw 13e and the second hook claw 19 in a locked state. Accordingly, there is no possibility that the first hook claw 13e and the second hook claw 19 are disengaged during the rotational operation of the rotary member 8.

In contrast, for example as shown in FIG. 39B, when a positional relationship between the pivotally supporting portion 13a of the rotation restricting portion 13 and the first hook claw 13e is right/left reversed, and when the second hook claw 19 is formed on the injector main body 5 in accordance with the reversed positional relationship, there is a possibility that the first hook claw 13e and the second hook claw 19 are disengaged during the rotational operation of the rotary member 8. Specifically, when the rotational force Fr is applied to the plunger 9 by the rotational operation of the rotary member 8, there is a case that the rotation restricting portion 13 is deformed or displaced by being pushed by the rotational force Fr, depending on the characteristics of a material constituting the injector main body 5 (including the rotation restricting portion 13). As a result, there is a possibility that the first hook claw 13e is displaced outwardly and disengaged from the second hook claw 19. Therefore, as shown in FIG. 39A, it is preferable that the rotational force Fr applied to the plunger 9 by the rotational operation of the rotary member 8 is applied in a direction to press the first hook claw 13e against the second hook claw 19.

Figures 39C, 39D:
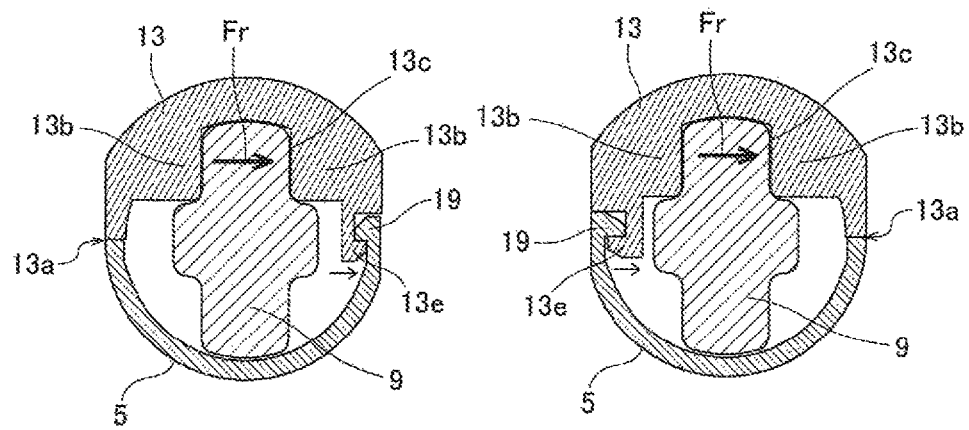

Further, as shown in FIG. 39C, it is also possible to employ a configuration in which the first hook claw 13e of the rotation restricting portion 13 is disposed relatively inside and the second hook claw 19 of the injector main body 5 is disposed relatively outside. In this configuration as well, the rotational force Fr applied to the plunger 9 by the rotational operation of the rotary member 8 is applied in a direction to press the first hook claw 13e against the second hook claw 19. Therefore, there is no possibility that the first hook claw 13e and the second hook claw 19 are disengaged during the rotational operation of the rotary member 8. Incidentally, as shown in FIG. 39D, when the positional relationship between the pivotally supporting portion 13a of the rotation restricting portion 13 and the first hook claw 13e is right/left reversed, and when the second hook claw 19 is formed on the injector main body 5 in accordance with the reversed positional relationship, there is a case that the rotation restricting portion 13 is deformed or displaced by being pushed by the rotational force Fr applied to the plunger 9. As a result, there is a possibility that the first hook claw 13e is pushed outwardly and disengaged from the second hook claw 19. Therefore, it is preferable to employ the configuration shown in FIG. 39C.

Note that the hook mechanism shown in FIGS. 39A to 39D can be applied to the first embodiment and the second embodiment described above, and in this case as well, it is preferable to employ the configuration shown in FIG. 39A or FIG. 39C.

(Configuration of the Plunger)

A pressing plate portion 9d is formed at the rear end portion of the plunger 9. The pressing plate portion 9d is a portion for pressing a thumb of a surgeon in a case of the operation by the push system, and is formed so as to protrude radially more than the plunger shaft 9a. In the pressing plate portion 9d, unevenness may be provided on the surface against which the surgeon's thumb is pressed, for anti-falloff purpose.

When the pressing plate portion 9d is provided at the rear end portion of the plunger 9 as described above, the operation by the push system becomes easy. Further, the rear end portion of the plunger 9 comes into contact with the thumb on a wider surface compared with the first embodiment. Therefore the load applied to the thumb at the time of pushing the plunger 9 is dispersed. Therefore, a burden on the thumb can be reduced.

The configuration in which the pressing plate portion 9d is provided at the rear end portion of the plunger 9, can be employed in the first embodiment and the second embodiment described above.

(Configuration of the Injection Tube)

Figure 29A:
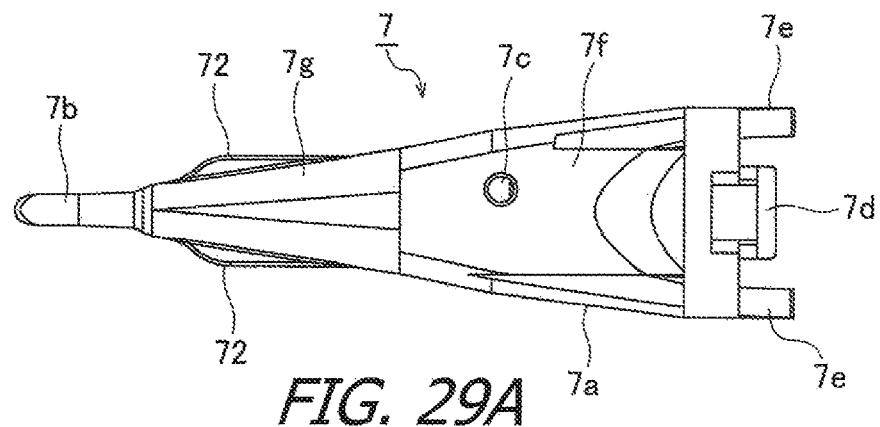
Figure 29B:
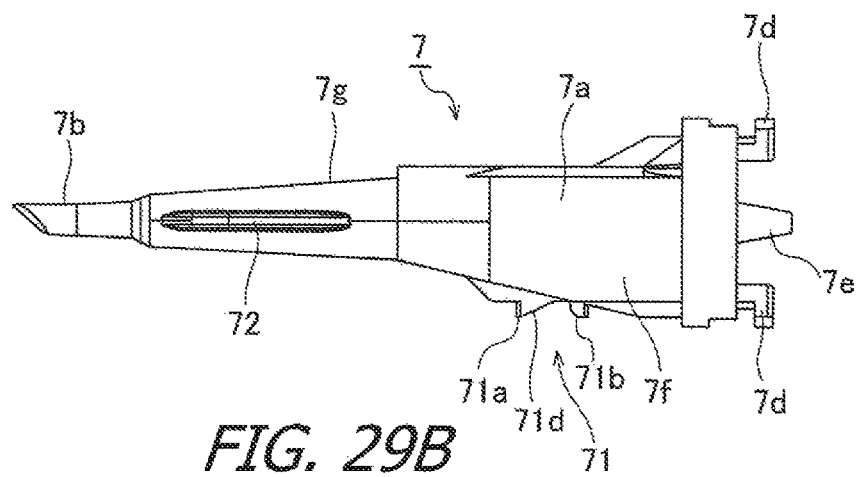
Figure 29C:
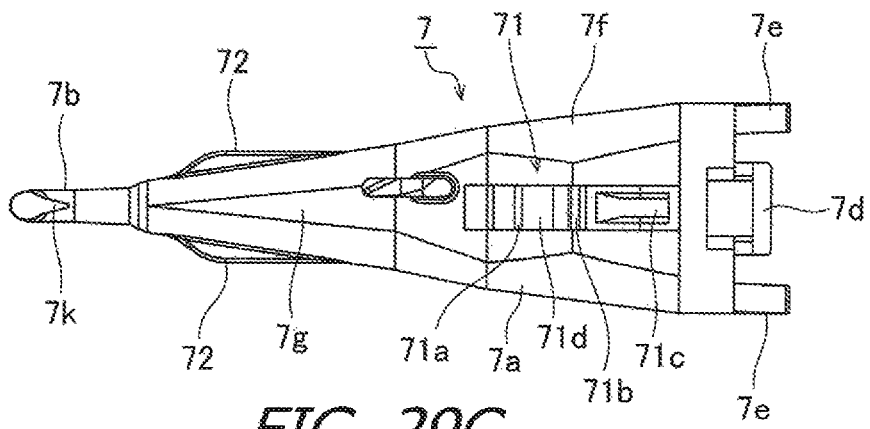
Figure 30A:
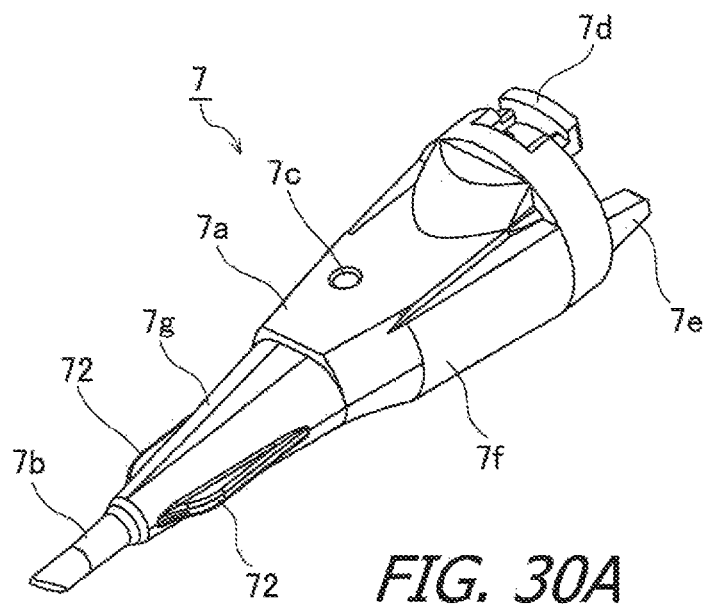
FIG. 30A is a perspective view of the injection tube as seen obliquely from above according to the third embodiment of the present invention.
Figure 30B:
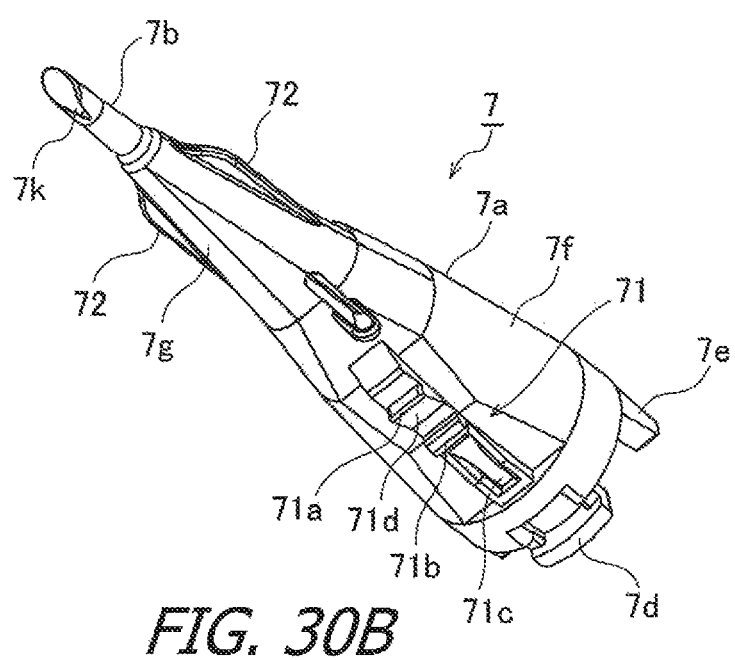
FIG. 30B is a perspective view as seen diagonally from below.

FIGS. 29A to 29C show a configuration of the injection tube according to the third embodiment of the present invention, wherein FIG. 29A is a plan view, FIG. 29B is a side view, and FIG. 29C is a bottom view. Further, FIG. 30A is a perspective view of the injection tube according to the third embodiment of the present invention as seen obliquely from above, and FIG. 30B is a perspective view as seen diagonally from below.

The injection tube 7 has a hollow injection tube main body 7a and a narrow tubular nozzle portion 7b, and an injection hole 7c is formed on the upper surface of the injection tube main body 7a. The injection tube main body 7a is divided into a first portion 7f and a second portion 7g. Further, the rear end portion of the injection tube main body 7a is opened, and a hook portion 7d and a wedge portion 7e are formed around the opening portion. A cutout portion 7k is formed in the nozzle portion 7b. The above points are similar to those of the first embodiment.

An engaged portion 71 is formed on a lower surface side of the first portion 7f of the injection tube main body 7a. Two small protrusions 71a, 71b and a recessed groove 71c are formed in the engaged portion 71. The small protrusion 71b is disposed between the small protrusion 71a and the recessed groove 71c in the axial direction of the injection tube 7. The small protrusion 71a has a slope 71d. The slope 71d has an inclination such that the protrusion amount of the small protrusion 71a is gradually increased toward the tip side of the injection tube 7.

A pair of right and left guide ribs 72 is formed, on both sides of the second portion 7g of the injection tube main body 7a. The pair of guide ribs 72 performs a guide function for relatively positioning the injection tube 7 and the attachment member 16 in the direction around the axis of the injection tube 7 when the attachment member 16 is attached to the injection tube 7. The pair of guide ribs 72 is formed so as to protrude like wings from both sides of the injection tube main body 7a (the second portion 7g).

(Configuration of the Attachment Member)

Figure 31A:
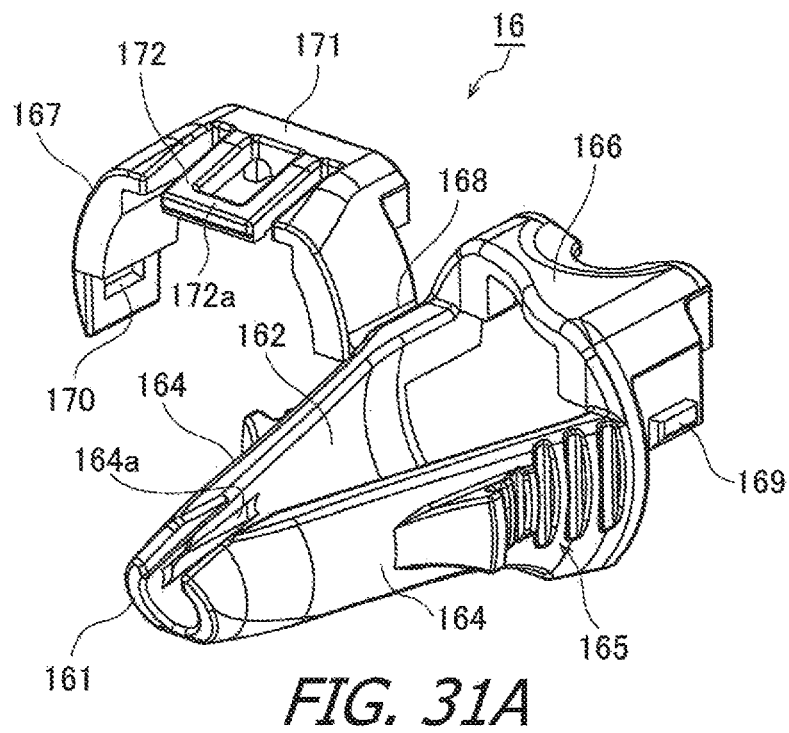
Figure 31B:
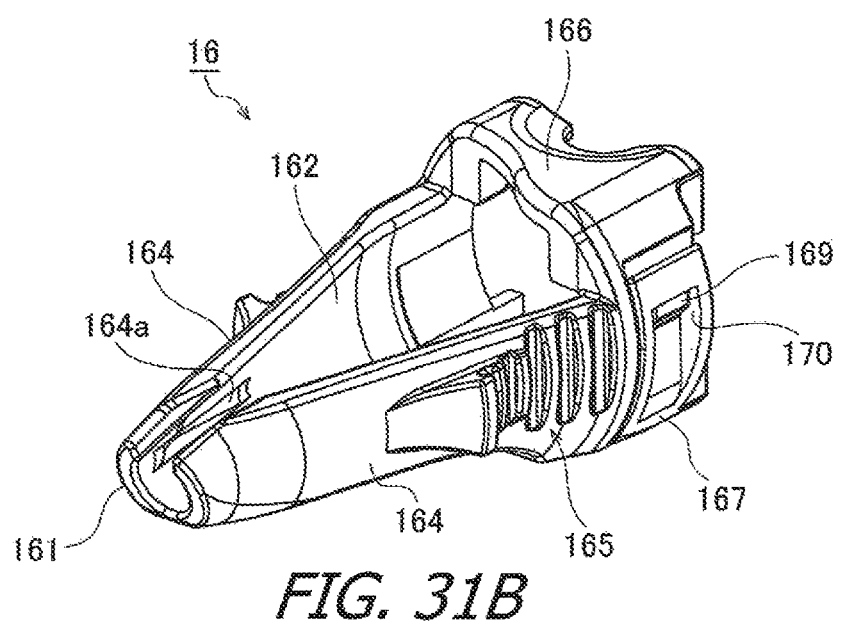
Figure 32A:
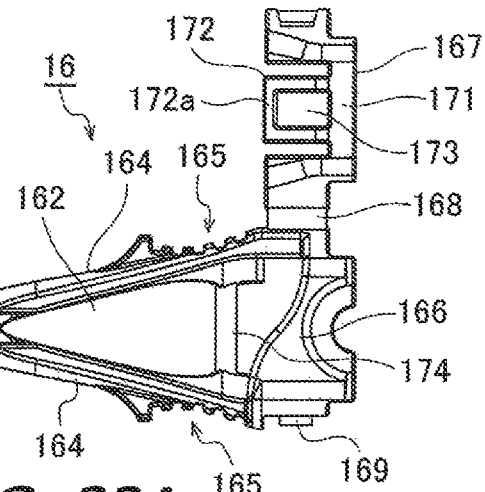
Figure 32B:
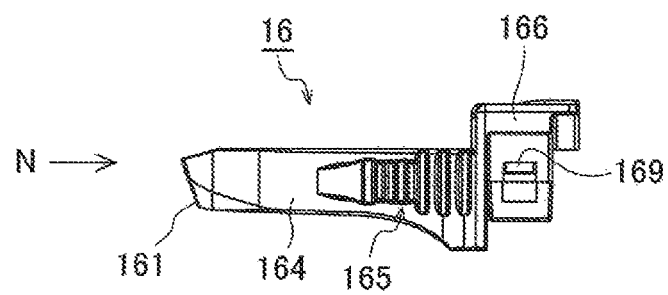
Figure 32C:
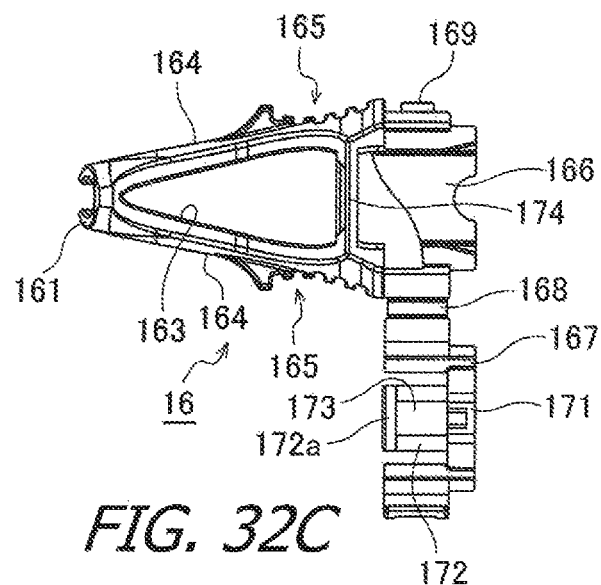
Figure 33:
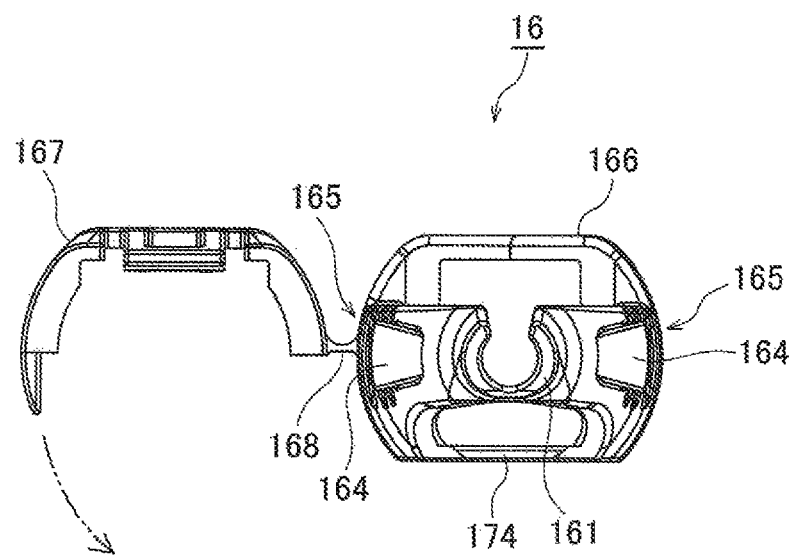
FIG. 33 is a view as seen from arrow N in FIG. 32B.

FIGS. 31A and 31B are perspective views of the attachment member according to a third embodiment of the present invention as seen obliquely from above, FIG. 31A shows the attachment member before being attached to the injection tube, and FIG. 31B shows the attachment member after being attached to the injection tube. Further, FIGS. 32A to 32C show a configuration of the attachment member according to the third embodiment of the present invention, wherein FIG. 32A is a plan view, FIG. 32B is a side view, and FIG. 32C is a bottom view. Further, FIG. 33 is a view as seen from arrow N in FIG. 32B. Note that FIGS. 32A to 32C show the attachment member before being attached to the injection tube.

As in the first embodiment, the attachment member 16 is a member that provides the nozzle insertion amount limiting function. The material of the attachment member 16 is preferably a resin, more preferably a transparent or translucent resin. The attachment member 16 is desirably made of an integrally molded product of resin. The attachment member 16 is a member separate from the injection tube 7, and is configured to be movable with respect to the injection tube 7. A movable direction of the attachment member 16 with respect to the injection tube 7 is an axial direction of the injection tube 7. Further, the third embodiment is configured as follows: although the attachment member 16 cannot be detached from the insertion tube 7 after the attachment member 16 is attached to the injection tube 7, the attachment member 16 can move in the axial direction of the injection tube 7 while the attachment member 16 is attached to the injection tube 7 (details will be described later).

A tip surface 161 as a protruding surface is formed at the tip part of the attachment member 16. The protruding surface of the attachment member 16 is a portion that directly comes into contact with a cornea when the intraocular lens is injected into the eye. Therefore, in order not to damage the cornea as much as possible, a body portion (excluding the portion of the protruding surface) of the attachment member 16 may be formed of hard resin, and the portion of the protruding surface may be formed of a soft resin such as silicone or urethane. The tip surface 161 as the protruding surface is formed in a shape (C shape) in which the upper part of an annular ring is cut out.

A viewing window 162 is formed in the upper part of the attachment member 16. A punched hole 163 is formed on the bottom of the attachment member 16. The viewing window 162 is formed to allow the state of the intraocular lens 4 moving inside of the injection tube 7 to be visually recognized from the outside, even when the attachment member 16 is attached to the injection tube 7. A width of the viewing window 162 is gradually narrowed from the rear end side toward the tip side of the attachment member 16 in accordance with a change in the width of the injection tube 7. The tip side of the viewing window 162 is opened without being closed and communicates with a cutout portion of the tip surface 161. Therefore, even when the attachment member 16 is attached to the injection tube 7, the whole part from the injection tube main body 7a of the injection tube 7 to the nozzle portion 7b can be viewed from the outside through the viewing window 162. Accordingly, when the intraocular lens 4 is pushed out through the nozzle portion 7b of the injection tube 7, it is possible to visually recognize the state of the intraocular lens 4 moving inside of the injection tube 7 without being disturbed by the attachment member 16.

Figure 34:
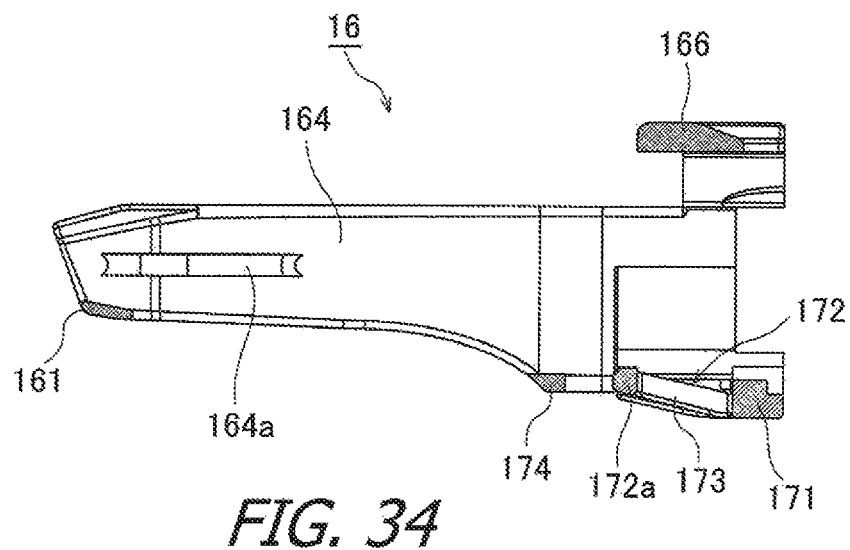
FIG. 34 is a longitudinal sectional view of the attachment member according to the third embodiment of the present invention, showing a state in which the engaging portion is closed.

A pair of left and right side plate portions 164 are provided on both sides of the attachment member 16. As shown in FIG. 34, a slit groove 164a is formed on the inner surface of each side plate portion 164. The slit groove 164a is formed corresponding to the guide rib 72 of the injection tube 7. Note that FIG. 34 is a longitudinal sectional view of the attachment member according to a third embodiment of the present invention, showing a state in which the engaging portion 167 is closed. Grip portions 165 are formed on the outer surface of each side plate portion 164. The grip portions 165 are provided on the left and right sides of the attachment member 16 in order to be able to grip the attachment member 16 with an index finger and a thumb when the surgeon or the like handles the attachment member 16. Each grip portion 165 has a concavo-convex structure so that a surgeon or the like can grip the attached member 16 easily.

A bridge portion 166 and an engaging portion 167 are provided at the rear portion of the attachment member 16. The bridge portion 166 is formed at an upper portion of the attachment member 16 so as to bridge between the pair of side plate portions 164. A part of the bridge portion 166 is formed by being bent into a waveform so as not to block the injection hole 7c when the attachment member 16 is attached to the injection tube 7. The bridge portion 166 is connected to the engaging portion 167 by a connecting portion 168. The connecting portion 168 is provided in one of the left and right directions. The connecting portion 168 is formed thin so as to have moderate flexibility. The engaging portion 167 is rotatably supported around the connecting portion 168 at the center (fulcrum) by utilizing the flexibility of the connecting portion 168. FIG. 33 shows a state in which the engaging portion 167 is opened, and from this state, by rotating the engaging portion 167 in a direction indicated by the two-dot chain line arrow in the figure, the engaging portion 167 can be closed. When the attachment member 16 is attached to the injection tube 7, by rotating the engaging portion 167 so as to close it, the engaging portion 167 can be engaged with the engaged portion 71.

A coupling claw 169 is formed in the bridge portion 166. The coupling claw 169 is formed to protrude on the side opposite to the connecting portion 168 in the left-right direction. Meanwhile, a coupling hole 170 corresponding to the coupling claw 169 is formed in the engaging portion 167. The coupling claw 169 and the coupling hole 170 serve as annularly coupling the bridge portion 166 and the engaging portion 167, by connecting the bridge portion 166 and the engaging portion 167 on the side opposite to the connecting portion 168. Specifically, the coupling claw 169 and the coupling hole 170 are engaged with each other and connected by rotating the engaging portion 167 so as to be closed, with the connecting portion 168 as a center. Thereby, the bridge portion 166 and the engaging portion 167 can be annularly coupled. When the attachment member 16 is attached to the injection tube 7, the bridge portion 166 is disposed on the upper side of the injection tube main body 7a (the first portion 7f), and the engaging portion 167 is disposed on the lower side of the injection tube main body 7a. Therefore, the injection tube main body 7a is surrounded by the bridge portion 166 and the engaging portion 167. Further, in a state in which the bridge portion 166 and the engaging portion 167 are coupled, their inner circumferential surfaces have a shape corresponding to the outer circumferential surface of the injection tube main body 7a.

The engaging portion 167 has a fixing piece 171 and a movable piece 172 extending forward from the fixing piece 171. A hole 173 is formed between the movable piece 172 and the fixing piece 171. The movable piece 172 has a bending property, with the connecting portion between the fixed piece 171 and the movable piece 172 as a fixed end and the tip part 172a of the movable piece 172 as a free end (referred to as "leaf spring property" hereafter). The fixing piece 171 and the movable piece 172 are formed corresponding to the small protrusions 71a and 71b and the recessed groove 71c constituting the engaged portion 71 of the injection tube 7. The tip part 172a of the movable piece 172 is configured to be able to get over the small protrusion 71a by moving along the slope 71d of the small protrusion 71a. Then, the tip part 172a of the movable piece 172 gets over the small protrusion 71a along the slope 71d, whereby the attachment member 16 moves forward, and the protrusion amount of the nozzle portion 7b is changed.

A coupling bar 174 is formed at a lower portion of the attachment member 16 so as to bridge between the pair of side plate portions 164. The coupling bar 174 is disposed so as to be opposed to the tip part 172a of the movable piece 172 when the engaging portion 167 is closed. In the axial direction of the attachment member 16, a punched hole 163 is formed in front of the coupling bar 174.

(Procedure for Attaching the Attachment Member)

Next, a procedure for attaching the attachment member 16 to the injection tube 7 will be described. Note that attachment of the attachment member 16 is performed in a manufacturing process (assembly process) of the intraocular lens injector 1.

Figure 35:
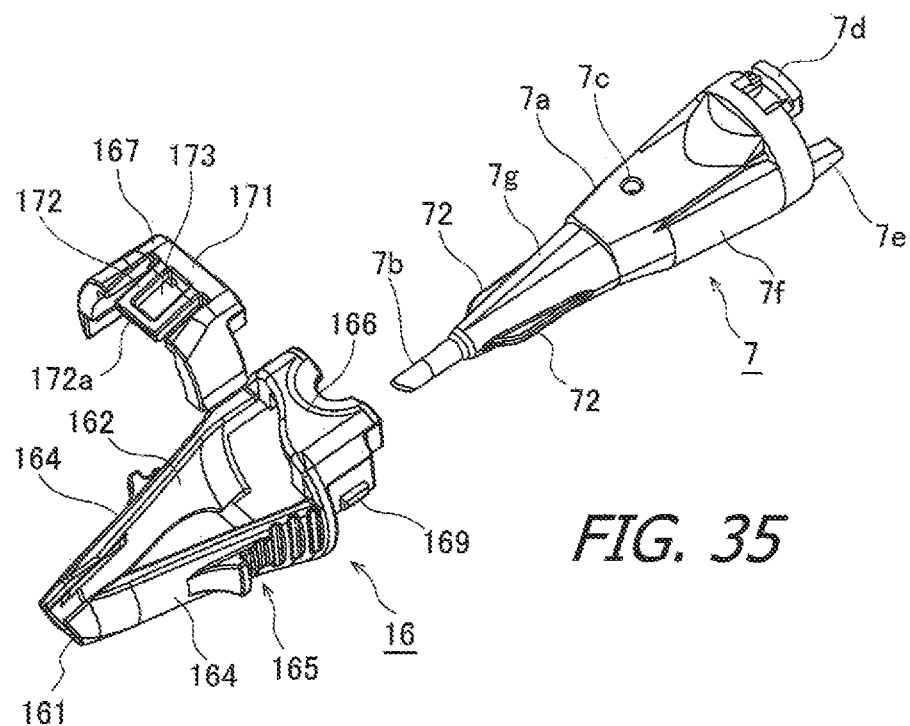
FIG. 35 is a perspective view (part 1) showing a procedure for attaching the attachment member according to the third embodiment of the present invention.

First, as shown in FIG. 35, the attachment member 16 with the engaging portion 167 opened, is disposed in front of the nozzle portion 7b of the injection tube 7.

Figure 36:
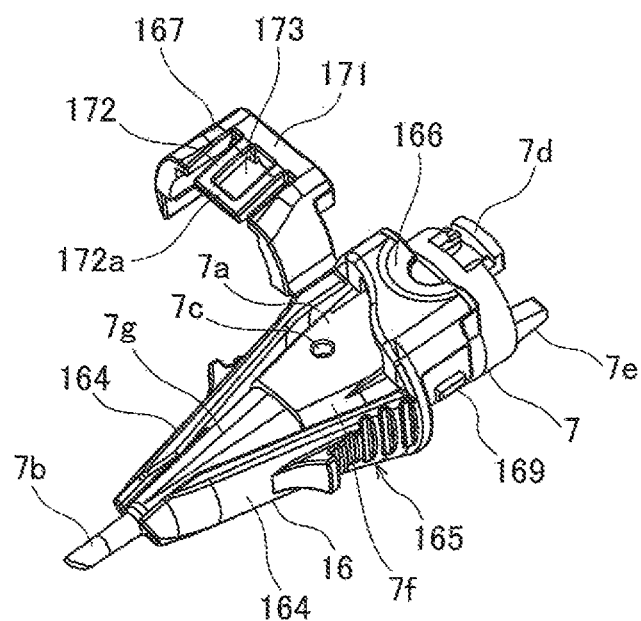
FIG. 36 is a perspective view (part 2) showing a procedure for attaching the attachment member according to the third embodiment of the present invention.

Next, as shown in FIG. 36, by bringing the attachment member 16 and the injection tube 7 relatively closer to each other, the attachment member 16 is put on the outside of the injection tube 7. At this time, the attachment member 16 is inserted to the rear end portion of the injection tube 7. Then, the nozzle portion 7b protrudes from the tip surface 161 of the attachment member 16 by a predetermined amount. Further, when the attachment member 16 is inserted into the injection tube 7, a pair of guide ribs 72 formed on the injection tube 7 is engaged with a pair of slit grooves 164a formed in the attachment member 16 so as to correspond to the pair of guide ribs 72. Thereby, the injection tube 7 and the attachment member 16 are positioned in the direction around the axis of the injection tube 7.

Next, by rotating the engaging portion 167 so as to be closed, with the connecting portion 168 of the attached member 16 as a center, the coupling hole 170 of the engaging portion 167 and the coupling claw 169 of the bridge portion 166 are fitted and connected to each other. Thereby, the bridge portion 166 and the engaging portion 167 are annularly coupled.

With the above procedure, the attachment member 16 can be attached to the injection tube 7. The attachment member 16 cannot be detached from the injection tube 7 after the attachment member 16 is attached to the injection tube 7. Namely, in the third embodiment of the present invention, the attachment member 16 cannot be detached from the injection tube 7. However, the attachment member 16 is configured to be movable with respect to the injection tube 7. This point will be described hereafter.

Figure 37:
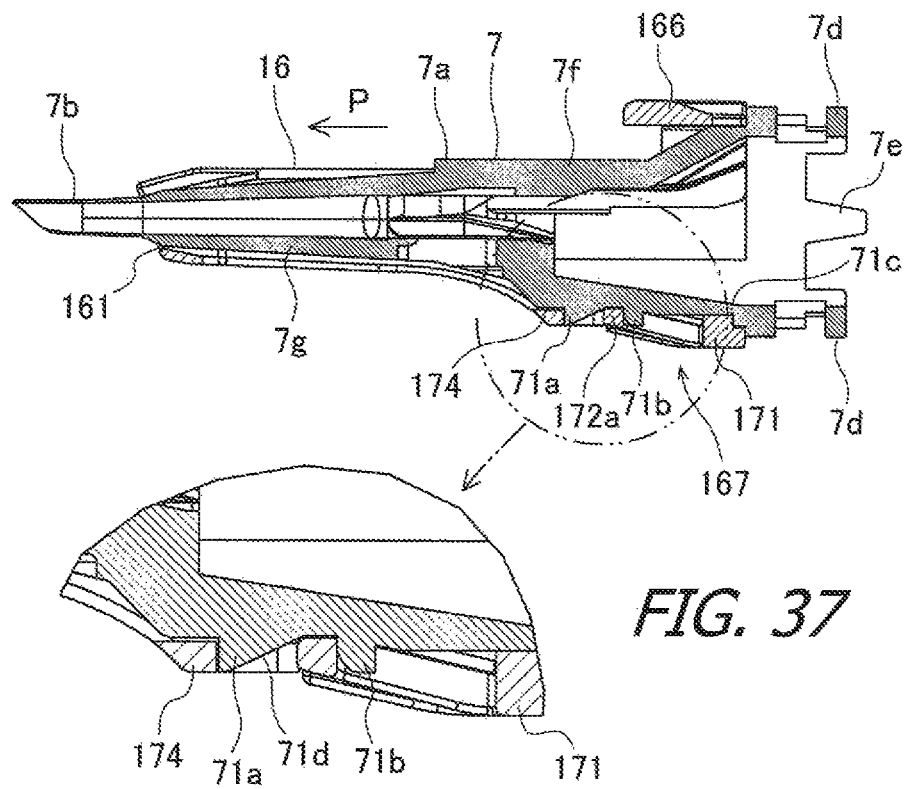
FIG. 37 is a longitudinal sectional view showing a state in which the attachment member is attached to the injection tube according to the third embodiment of the present invention.

First, as described above, when the attachment member 16 is attached to the injection tube 7, the positional relationship between the small protrusion 71a, the small protrusion 71b, the recessed groove 71c of the injection tube 7, and the fixing piece 171, the movable piece 172, the coupling bar 174 of the attachment member 16, is as shown in FIG. 37. Namely, the small protrusion 71a is disposed between the tip part 172a of the movable piece 172 and the coupling bar 174, and the small protrusion 71b is disposed between the tip part 172a of the movable piece 172 and the fixing piece 171, in the axial direction of the injection tube 7. Further, the tip part 172a of the movable piece 172 is disposed in contact (or close proximity) to a front surface of the small protrusion 71b adjacent to the slope 71d of the small protrusion 71a, and the coupling bar 174 is disposed in contact (or close proximity) to an entire surface of the small protrusion 71a.

When the attachment member 16 is moved from the above state, first, a surgeon or the like grips a pair of gripping portions 165 formed on both sides of the attachment member 16 with two fingers (usually an index finger and a thumb). Next, a force in a direction P is applied to the attachment member 16 while gripping the pair of gripping portions 165 with fingers. Then, the movable piece 172 formed at the lower part of the attachment member 16, is deformed due to the leaf spring property of the movable piece 172 itself, while contacting the slope 71d of the small protrusion 71a of the injection tube 7. Then, the tip part 172a of the movable piece 172 moves along the slope 71d, and the movable piece 172 returns to an original shape due to its own leaf spring property when getting over the protruding end portion of the small protrusion 71a.

Figure 38:
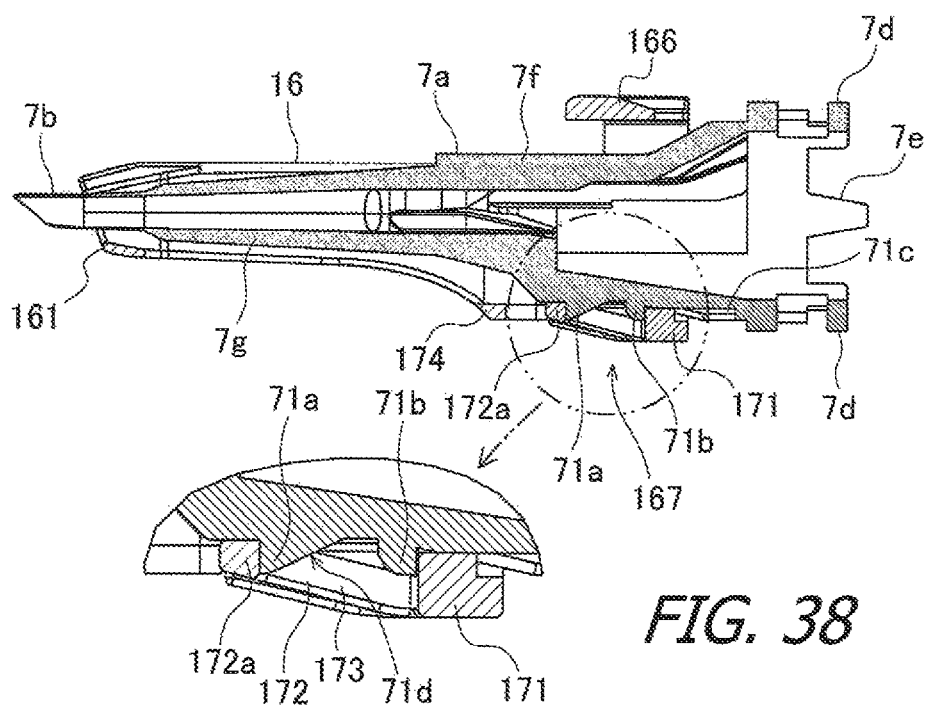
FIG. 38 is a longitudinal sectional view showing a state in which the attachment member attached to the injection tube is moved in an axial direction according to the third embodiment of the present invention.

Thereby, the positional relationship between the small protrusion 71a, the small protrusion 71b, the recessed groove 71c of the injection tube 7, and the fixing piece 171, the movable piece 172, the coupling bar 174 of the attachment member 16, is as shown in FIG. 38. Namely, the small protrusion 71a is disposed between the tip part 172a of the movable piece 172 and the fixing piece 171, and the small protrusion 71*b* is also disposed between the tip part 172*a* of the movable piece 172 and the fixing piece 171 in the axial direction of the injection tube 7. Further, the tip part 172*a* of the movable piece 172 is disposed in contact (or close proximity) to the front surface of the small protrusion 71*a*, and the fixing piece 171 is disposed in contact (or close proximity) to the rear surface of the small protrusion 71*b*.

As described above, in this embodiment, the attachment member 16 can move in the axial direction of the injection tube 7, while the attachment member 16 is attached to the injection tube 7. Therefore, the protrusion amount of the nozzle portion 7*b* can be changed, while the attachment member 16 is attached to the injection tube 7. Thereby, the surgeon who prefers the procedure for inserting the nozzle portion 7*b* deeply into the incisional wound of an eyeball, uses the intraocular lens injector 1 in a state shown in FIG. 37, and the surgeon who prefers the procedure for shallowly inserting the nozzle portion 7*b*, can use the intraocular lens injector 1 in a state shown in FIG. 38. Accordingly, the surgeon performing the cataract surgery can selectively use the intraocular lens injector 1 according to the procedure of his/her choice.

Note that the third embodiment employs the configuration in which the protrusion amount of the nozzle portion 7*b* can be adjusted in two stages by allowing the attachment member 16 to move in the axial direction of the injection tube 7. However, the present invention is not limited to this configuration, and it is also acceptable to employ a configuration in which the protrusion amount of the nozzle portion 7*b* can be adjusted in multiple stages of three or more stages.

Further, the third embodiment employs the configuration in which the attachment member 16 cannot be returned to the position (backward) before the movement, due to the contact between the tip part 172*a* of the movable piece 172 and the small protrusion 71*a*, after the attachment member 16 attached to the injection tube 7 is moved forward. However, the present invention is not limited to this configuration, and it is also acceptable to employ a configuration in which the attachment member 16 can be returned to its original position.

<Modified Example, Etc>

The technical scope of the present invention is not limited to the embodiment described above but includes various modes and modifications as far as the specific effects obtained by the constituent features of the invention and combinations thereof can be derived.

For example, in the above embodiment, the plunger 9 and the rod 10 are formed as separate members, but they may be formed as an integral structure.

Further, in the above embodiment, the viewing window 16*g* is formed in a state in which a part of the attachment member 16 is cut out. However, the present invention is not limited thereto, and a hole (not shown) having a proper size may be formed in a part of the attachment member 16, and this hole may be used as a viewing window.

Further, in the above embodiment, the injector main body 5 and the injection tube 7 are mutually assembled to form a hollow body. However, the hollow body may have an integral structure (such as an integrally molded product of resin).

Further, in the above embodiment, the slider 6 is included in one of the components of the intraocular lens injector 1. However, the slider 6 is an auxiliary member for folding the intraocular lens 4 into a desired shape, and is not always necessary to inject the intraocular lens 4 into the eye. Therefore, it is not necessary to provide the slider 6, as long as the intraocular lens 4 can be folded into a desired shape merely by pushing out the intraocular lens 4 using the rod 10, for example by devising the configuration of the lens installing portion 11 in the injector main body 5 and the configuration of the tip of the rod 10.

DESCRIPTION OF SIGNS AND NUMERALS

1 Intraocular lens injector
4 Intraocular lens
5 Injector main body
7 Injection tube
7*b* Nozzle portion
7*k* Cutout portion
7*m* Locking claw
8 Rotary member
9 Plunger
9*c* Second threaded portion
10 Rod
11 Lens installing portion
13 Rotation restricting portion
13*d* Anti-falloff portion
16 Attachment member
16*a* Tip surface
16*b* Engaging portion
16*g* Viewing window
16*i* Tapered portion
16*j* Tongue piece
16*k* Engagement hole

The invention claimed is:

1. An intraocular lens injector for injecting an intraocular lens into an eye, comprising:
   a hollow body having a lens installing portion including a surface configured to have an intraocular lens installed thereon;
   a rotary member having a first threaded portion with threads formed thereon, and attached to a rear end portion of the hollow body, rotatably around an axis of the hollow body;
   a plunger having a second threaded portion with threads formed thereon, and configured to move through the hollow body in an axial direction of the hollow body; and
   a pushing member configured to push out an intraocular lens from the lens installing portion by moving through the hollow body in the axial direction of the hollow body together with the plunger,
   wherein a tip side of the plunger is inserted into the hollow body in a state in which the threads of the first threaded portion mesh directly with the threads of the second threaded portion, and a rear end side of the plunger is disposed in a state of protruding backward of the rotary member.

2. The intraocular lens injector according to claim 1, wherein the hollow body has a rotation restricting portion including a surface configured to restrict rotation of the plunger.

3. The intraocular lens injector according to claim 2, wherein the rotation restricting portion is provided rotatably so as to open and close an opening formed on an outer wall of the hollow body, and at least a part of the rotation restricting portion is shielded by the rotary member.

4. The intraocular lens injector according to claim 1, wherein the hollow body has an anti-falloff portion with a surface positioned to engage a portion of the plunger and prevent the plunger from falling off from the hollow body.

5. The intraocular lens injector according to claim 1, wherein a taper angle of a rear side of the second threaded portion is 5° or more and 15° or less.

6. The intraocular lens injector according to claim 1, wherein a pressing plate portion is provided at the rear end side of the plunger.

7. The intraocular lens injector according to claim 1, further comprising:
an intraocular lens installed on the lens installing portion.

8. An intraocular lens injector, comprising:
a hollow body, defining a rear end portion, a front end portion, an axis and an axial direction, configured to receive an intraocular lens;
a nozzle associated with the front end portion of the hollow body;
a rotary member, having a first threaded portion with threads, rotatably attached to the hollow body rear end portion and rotatable around the hollow body axis;
a plunger, defining a rear end located rearward of the rotary member, having a second threaded portion with threads that are in direct contact with the threads of the first threaded portion, and configured to move through the hollow body in the axial direction; and
a rod, operably connected to the plunger, configured to push an intraocular lens through the nozzle as the plunger moves in the axial direction.

9. The intraocular lens injector according to claim 8, wherein the hollow body has a rotation restricting portion including a surface configured to restrict rotation of the plunger.

10. The intraocular lens injector according to claim 9, wherein
the hollow body includes an outer wall defining an opening;
the rotation restricting portion is configured to cover the opening; and
at least a part of the rotation restricting portion is shielded by the rotary member.

11. The intraocular lens injector according to claim 8, wherein the hollow body has an anti-falloff portion with a surface positioned to engage a portion of the plunger and prevent the plunger from falling off from the hollow body.

12. The intraocular lens injector according to claim 8, wherein the rear end of the plunger includes a plate.

13. The intraocular lens injector according to claim 8, further comprising:
an intraocular lens stored on a portion of the hollow body.

14. An intraocular lens injector, comprising:
a hollow body, defining a rear end portion, a front end portion, an axis and an axial direction, configured to receive an intraocular lens;
a nozzle associated with the front end portion of the hollow body;
a rotary member, having a first threaded portion, attached to the hollow body rear end portion and rotatable around the hollow body axis;
a plunger, defining a rear end located rearward of the rotary member, having a second threaded portion that defines a rear side taper angle that is 5° or more and 15° or less and is in direct contact with the first threaded portion, and configured to move through the hollow body in the axial direction; and
a rod, operably connected to the plunger, configured to push an intraocular lens through the nozzle as the plunger moves in the axial direction.

15. An intraocular lens injector, comprising:
a hollow body, defining a rear end portion, a front end portion, an axis and an axial direction, configured to receive an intraocular lens;
a nozzle associated with the front end portion of the hollow body;
a rotary member, having a first threaded portion with threads, rotatably attached to the hollow body rear end portion and rotatable around the hollow body axis;
a plunger, defining a rear end located rearward of the rotary member, having a second threaded portion with threads that are meshed directly with the threads of the first threaded portion, configured to move through the hollow body in the axial direction, and prevented from rotating relative to the hollow body as it moves in the axial direction; and
a rod, operably connected to the plunger, configured to push an intraocular lens through the nozzle as the plunger moves in the axial direction.

16. The intraocular lens injector according to claim 15, wherein the hollow body has a rotation restricting portion including a surface configured to restrict rotation of the plunger.

17. The intraocular lens injector according to claim 15, wherein the hollow body has an anti-falloff portion with a surface positioned to engage a portion of the plunger and prevent the plunger from falling off from the hollow body.

18. The intraocular lens injector according to claim 15, wherein the threads of the second threaded portion define a rear side taper angle that is 5° or more and 15° or less.

19. The intraocular lens injector according to claim 15, wherein the rear end of the plunger includes a plate.

20. The intraocular lens injector according to claim 15, further comprising:
an intraocular lens stored on a portion of the hollow body.

21. An intraocular lens injector, comprising:
a hollow body defining a rear end portion, a front end portion, an axis and an axial direction, and that includes a guide groove and is configured to receive an intraocular lens;
a nozzle associated with the front end portion of the hollow body;
a rotary member, having a first threaded portion, attached to the hollow body rear end portion and rotatable around the hollow body axis;
a plunger, defining a rear end located rearward of the rotary member, having a second threaded portion meshed with the first threaded portion, configured to move through the hollow body in the axial direction, and having at least a portion that defines a cruciform shape in cross-section and is located in the guide groove to prevent the plunger from rotating relative to the hollow body as it moves in the axial direction; and
a rod, operably connected to the plunger, configured to push an intraocular lens through the nozzle as the plunger moves in the axial direction.

* * * * *